US010235620B2

(12) United States Patent
Suskind et al.

(10) Patent No.: US 10,235,620 B2
(45) Date of Patent: *Mar. 19, 2019

(54) GUIDED PERSONAL COMPANION

(71) Applicant: The Affinity Project, Inc., Cambridge, MA (US)

(72) Inventors: Ronald Steven Suskind, Cambridge, MA (US); John Nguyen, Lexington, MA (US); Stuart R. Patterson, Hingham, MA (US); Stephen R. Springer, Needham, MA (US); Mark Alan Fanty, Norfolk, MA (US)

(73) Assignee: The Affinity Project, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/468,727

(22) Filed: Mar. 24, 2017

(65) Prior Publication Data

US 2017/0220922 A1    Aug. 3, 2017

Related U.S. Application Data

(63) Continuation of application No. 15/015,891, filed on Feb. 4, 2016, now Pat. No. 9,710,613, which is a
(Continued)

(51) Int. Cl.
*G06N 3/00* (2006.01)
*G16H 40/63* (2018.01)
(Continued)

(52) U.S. Cl.
CPC .............. *G06N 3/006* (2013.01); *G06F 19/00* (2013.01); *G06F 19/3481* (2013.01); *G09B 5/06* (2013.01);
(Continued)

(58) Field of Classification Search
None
See application file for complete search history.

(56) References Cited

U.S. PATENT DOCUMENTS 6,230,111 B1 * 5/2001 Mizokawa ............. G06N 3/004
345/473
6,731,307 B1 * 5/2004 Strubbe .................. G06N 3/004
704/E17.002

(Continued)

FOREIGN PATENT DOCUMENTS

CN          104483847           4/2015
CN          104483847  A  *    4/2015
(Continued)

OTHER PUBLICATIONS

U.S. Appl. No. 15/166,333, filed May 27, 2016.
(Continued)

*Primary Examiner* — Paulinho E Smith
(74) *Attorney, Agent, or Firm* — Fish & Richardson P.C.

(57) ABSTRACT

The operation of an application on a first device may be guided by a user operating a second device. The application on the first device may present a character on a display of the first device and obtain an audio signal of speech of a user of the first device. Audio data may be transmitted to the second device and corresponding audio may be played from speakers of the second device. The second device may present suggestions of phrases to be spoken by the character displayed on the first device. A user of the second device may select a phrase to be spoken by the character. Phrase data may be transmitted to the first device, and the first device may generate audio of the character speaking the phrase using a text-to-speech voice associated with the character.

22 Claims, 10 Drawing Sheets

Related U.S. Application Data continuation-in-part of application No. 14/571,472, filed on Dec. 16, 2014, now Pat. No. 9,704,103.

(60) Provisional application No. 62/281,785, filed on Jan. 22, 2016.

(51) Int. Cl.
| | |
|---|---|
| *G16H 50/20* | (2018.01) |
| *G06F 19/00* | (2018.01) |
| *H04M 1/725* | (2006.01) |
| *G09B 5/06* | (2006.01) |
| *G09B 5/14* | (2006.01) |
| *G09B 19/04* | (2006.01) |
| *G10L 13/04* | (2013.01) |
| *G10L 13/00* | (2006.01) |

(52) U.S. Cl.
CPC ............... *G09B 5/065* (2013.01); *G09B 5/14* (2013.01); *G09B 19/04* (2013.01); *G10L 13/043* (2013.01); *G16H 40/63* (2018.01); *G16H 50/20* (2018.01); *H04M 1/72544* (2013.01); *G10L 13/00* (2013.01)

(56) References Cited

U.S. PATENT DOCUMENTS

| | | | |
|---|---|---|---|
| 6,795,808 B1* | 9/2004 | Strubbe | G06F 17/30702 704/270 |
| 7,606,714 B2 | 10/2009 | Williams | |
| 9,704,103 B2 | 7/2017 | Suskind et al. | |
| 9,710,613 B2 | 7/2017 | Susldnd et al. | |
| 9,802,125 B1 | 10/2017 | Suskind et al. | |
| 2004/0147814 A1* | 7/2004 | Zancho | H04M 19/04 600/300 |
| 2005/0187781 A1* | 8/2005 | Christensen | H04L 51/04 709/207 |
| 2008/0077277 A1* | 3/2008 | Park | G06N 3/008 700/245 |
| 2009/0055019 A1* | 2/2009 | Stiehl | B25J 9/1671 700/249 |
| 2009/0319459 A1* | 12/2009 | Breazeal | G06K 9/00335 706/46 |
| 2010/0198645 A1* | 8/2010 | Heiss | G06Q 10/10 709/206 |
| 2012/0101847 A1 | 4/2012 | Johnson | |
| 2012/0295510 A1* | 11/2012 | Boeckle | A63H 3/28 446/72 |
| 2013/0090949 A1 | 4/2013 | Tibebu | |
| 2013/0316324 A1 | 11/2013 | Hoffmann | |
| 2013/0326386 A1 | 12/2013 | Vendrell | |
| 2014/0018382 A1* | 1/2014 | DeLack | A61K 31/40 514/280 |
| 2014/0150791 A1 | 6/2014 | Birnkrant | |
| 2014/0156645 A1 | 6/2014 | Brust et al. | |
| 2014/0212854 A1* | 7/2014 | Divakaran | G09B 25/00 434/236 |
| 2014/0347265 A1* | 11/2014 | Aimone | G09G 3/003 345/156 |
| 2015/0170531 A1 | 6/2015 | Hu et al. | |
| 2015/0294595 A1 | 10/2015 | Hu et al. | |
| 2015/0336276 A1* | 11/2015 | Song | B25J 11/001 700/253 |
| 2016/0005326 A1* | 1/2016 | Syrmis | G09B 7/00 434/362 |
| 2016/0117953 A1 | 4/2016 | Lluch | |
| 2016/0171387 A1 | 6/2016 | Suskind et al. | |
| 2016/0171971 A1 | 6/2016 | Suskind et al. | |
| 2017/0200075 A1 | 7/2017 | Suskind et al. | |

FOREIGN PATENT DOCUMENTS

| | | | | |
|---|---|---|---|---|
| JP | | 2012-93972 | | 5/2012 |
| JP | | 2012093972 A * | | 5/2012 |
| JP | | 5539842 | | 7/2014 |
| WO | WO 2013/166146 | | | 11/2013 |
| WO | WO 2013166146 A1 * | | 11/2013 | ............. G06Q 10/10 |
| WO | WO 2016/099827 | | | 6/2016 |

OTHER PUBLICATIONS

U.S. Appl. No. 14/571,472, filed Dec. 16, 2014.
U.S. Appl. No. 15/015,891, filed Feb. 4, 2016.
U.S. Appl. No. 61/916,701, filed Dec. 16, 2013, Hu et al.
Acapela Group, "Voice synthesis—Text to Speech | voice solutions" [online], [retrieved on Dec. 2, 2014]. Retrieved from the Internet: http://www.acapela-group.com/, 4 pages.
AITalk® Customer Voice, "Original Voice Dictionary Creating Service" [online], [retrieved on Dec. 2, 2014]. Retrieved from the Internet: http://www.ai-j.jp/english/product/customvoice.html, 2 pages.
Bemelmans et al., "The Potential of Socially Assistive Robotics in Care of Elderly, a Systematic Review," 2011, Third International Conference HRPR 2010, pp. 83-89.
Bohus et al., "Sony, I Didn't Catch That!—An Investigation of Non-understanding Errors and Recovery Strategies" [online], [retrieved on Dec. 2, 2014]. Retrieved from the Internet: http://www.cs.cmu.edu/~dbohus/docs/nonu_final.pdf ,16 pages.
CereProc, "Voice Creations FAQs" [online], [retrieved on Dec. 2, 2014]. Retrieved from the Internet: https://www.cereproc.com/en/support/faqs/voicecreation, 3 pages.
Cleverscript, "Create a clever script" (conversational AI engine by Existor Ltd © 2012-2014) [online], [retrieved on Dec. 2, 2014]. Retrieved from the Internet: www.cleverscript.com, 2 pages.
Cleverscript, "Manual and Tutorial" [online], [retrieved on Dec. 2, 2014]. Retrieved from the Internet: http://www.cleverscript.com/CSL/CleverScriptManual.pdf, 76 pages.
Existor, "Evie—Electronic Virtual Interactive Entity—Artificial Intelligence is communication" [online], [retrieved on Dec. 2, 2014]. Retrieved from the Internet: http://www.existor.com, 1 page.
Ezzat et al., "Trainable Videorealistic Speech Animation" Massachusetts Institute of Technology [online], [retrieved on Dec. 2, 2014]. Retrieved from the Internet: http://cbcl.mit.edu/cbcl/publications/ps/siggraph02.pdf, 11 pages.
Festvox, "Transform" [online], [retrieved on Dec. 2, 2014]. Retrieved from the Internet: http://www.festvox.org/transform/, 2 pages.
iSpeech, "Powerful Speech Platform" [online], [retrieved on Dec. 2, 2014]. Retrieved from the Internet: http://www.ispeech.org, 7 pages.
Hamilton, "Eugene Goostman versus Siri" (Jun. 10, 2014) [online], [retrieved on Mar. 16, 2016]. Retrieved from the Internet: http://www.laurahamilton.com/eugene-goostman-versus-siri, 3 pages.
Levy, "Siri's Inventors Are Building a Radical New AI that Does Anything You Ask" (Aug. 12, 2014) [online], [retrieved on Mar. 16, 2016]. Retrieved from the Internet: http://www.wired.com/2014/08/viv/, 2 pages.
Leuski et al., "NPCEditor: A Tool for Building Question-Answering Characters" [online], [retrieved on Dec. 2, 2014]. Retrieved from the Internet: http://people.ict.usc.edu/~leuski/publications/papers/npceditor.pdf, 8 pages.
Massachusetts Institute of Technology, "Scientists collaborate internationally to identify the neural mechanisms and possible benefits of 'Affinity Therapy' in children with autism" (Apr. 24, 2014) [online], [retrieved on Dec. 2, 2014]. Retrieved from the Internet: https://iacc.hhs.gov/non-iacc-events/2014/nimh_lecture_ron suskind_042414.pdf, 1 page.
Pappu et al., "Predicting Tasks in Goal-Oriented Spoken Dialog Systems using Semantic Knowledge Bases" *Proceedings of the SIGDIAL 2013 Conference*, pp. 242-250 (Aug. 22-24, 2013) [online], [retrieved on Dec. 2, 2014]. Retrieved from the Internet: https://aclweb.org/anthology/W/W13/W13-4038.pdf, 9 pages.
Screaming Bee Inc., "MorphVOX Pro Voice Change" [online], [retrieved on Dec. 2, 2014]. Retrieved from the Internet: http://www.screamingbee.com/, 1 page.
SitePal, "Text-to-Speech" [online], [retrieved on Dec. 2, 2014]. Retrieved from the Internet: http://www.sitepal.com/ttswidgetdemo/, 1 page.

(56) References Cited

OTHER PUBLICATIONS

Strannegard et al., "A General System for Learning and Reasoning in Symbolic Domains" [online], [retrieved on Dec. 2, 2014]. Retrieved from the Internet: http://agi-conf.org/2014/wp-content/uploads/2014/08/strannegard-general-agi14.pdf, 12 pages.
Suskind, "Life, Animated: A Story of Sidekicks, Heroes, and Autism," Apr. 2014, 358 pages.
The New York Times, "Inside the Mind of a Child with Autism," written by Benedict Carey on Apr. 7, 2014 [online], [retrieved on Dec. 2, 2014]. Retrieved from the Internet: http://well.blogs.nytimes.com/2014/04/07/inside-the-mind-of-a-child-with-autism/?_r=0, 3 pages.
Wired.Co.Uk, "IBM reveals 'brain-like' chip with 4,096 cores," written by Daniela Hernandez on Aug. 8, 2014 [online], [retrieved on Dec. 2, 2014]. Retrieved from the Internet: http://www.wired.co.uk/news/archive/2014-08/08/ibm-brain-like-chip, 8 pages.
Yale Daily News, "Suskind sparks autism research," written by Eddy Wang on Apr. 15, 2014 [online], [retrieved on Dec. 2, 2014]. Retrieved from the Internet: http://yaledailynews.com/blog/2014/04/15/suskind-sparks-autism-research/, 2 pages.
International Search Report and Written Opinion for App. Ser. No. PCT/US15/62416, dated Feb. 5, 2016, 11 pages.
U.S. Appl. No. 14/571,472, Suskind et al., filed Dec. 16, 2014.
U.S. Appl. No. 15/015,891, Suskind et al., filed Feb. 4, 2016.
U.S. Appl. No. 15/166,333, Suskind et al., filed May 27, 2016.
U.S. Appl. No. 15/166,507, Suskind et al., filed May 27, 2016.
U.S. Appl. No. 61/916,701, Hu et al., filed Dec. 16, 2013.
International Preliminary Report on Patentability for App. Ser. No. PCT/US15/62416, dated Jun. 20, 2017, 8 pages.
U.S. Appl. No. 15/468,218, filed Mar. 24, 2017.
U.S. Appl. No. 15/166,507, filed May 27, 2016.
U.S. Appl. No. 14/571,472, filed Dec. 16, 2014 Patented Jul. 11, 2017.
U.S. Appl. No. 15/468,218, filed Mar. 24, 2017 Published.
U.S. Appl. No. 15/015,891, filed Feb. 4, 2016 Patented Jul. 18, 2017.
U.S. Appl. No. 15/166,333, filed May 27, 2016 Patented Oct. 11, 2017.
U.S. Appl. No. 15/166,507, filed May 27, 2016 Pending.

\* cited by examiner

GUIDED PERSONAL COMPANION

CROSS-REFERENCES TO RELATED APPLICATIONS

This application is a continuation (and claims the benefit of priority under 35 USC 120) of U.S. patent application Ser. No. 15/015,891, filed on Feb. 4, 2016, which is a continuation-in-part of U.S. patent application Ser. No. 14/571,472, filed on Dec. 16, 2014. This application claims the benefit of U.S. Provisional Patent Application No. 62/281,785, filed on Jan. 22, 2016. The contents of these applications are hereby incorporated in their entirety.

BACKGROUND

Individuals with special needs, such as children with autism, may find it difficult to interact socially with other people, such as their parents, friends, and people they are meeting for the first time. These special needs individuals may have an easier time communicating with a computer-generated personal companion, such as personal assistants on smart phones. While the special needs individual may be able to communicate more easily with a computer-generated personal companion, the personal companion may have limited capabilities and may not be able to provide functionality to assist the special needs individual. What is needed is a personal companion that is specifically adapted to communicate with the special needs individual and also assist the special needs individual with tasks in his daily life.

BRIEF DESCRIPTION OF THE FIGURES

The invention and the following detailed description of certain embodiments thereof may be understood by reference to the following figures:

FIG. 3B illustrates an example display of a Coach device for guiding a personal companion when the Hero is not available.

FIG. 3C illustrates an example display of a Coach device for guiding a personal companion when the Hero is available.

FIG. 3D illustrates an example display of a Coach device for guiding a companion assistant with a transcript.

DETAILED DESCRIPTION

Described herein are techniques for assisting a special needs individual, who we will refer to as the "Hero," in learning life skills. The Hero may have difficulty in interacting with people and may be reluctant to speak or have difficulties when communicating with another person. For example, the Hero may have autism, attention deficit disorder, or Alzheimer's disease. The Hero may have an easier time communicating with a computer-generated character that is presented on a device, such as a smartphone. For example, the Hero may find it easier to speak to a virtual personal assistant, such as Apple's Siri, than to speak to another person. In some implementations, the Hero may be a neuro-typical person and not have any special needs.

While the Hero may have an easier time communicating with an automated personal assistant, the personal assistant may not be particularly helpful in helping the Hero learn skills associated with emotional and physical regulation, social skills, executive functioning, interpersonal communication, and other aspects of our social culture that are typically not taught explicitly to those without special needs. We will refer to the foregoing skills as "life skills." What is needed is a computer-generated character that can interact with the Hero but also help the Hero learn life skills. In some implementations, a Coach (described in greater detail below) may be able to help guide how the computer-generated character interacts with the Hero. For example, the Coach may be parent or caretaker, and the Coach may be able to control or influence the words spoken by the computer-generated character.

The computer-generated character will be referred to herein as a personal companion or a Sidekick (Sidekick and Sidekicks are trademarks of The Affinity Project). A Sidekick may be an existing cartoon character, such as Mickey Mouse, or may be a newly created character created specifically for the purpose of communicating with a particular Hero or Heroes in general. A Sidekick has an associated appearance, personality, and voice.

Individuals who guide how the Sidekick interacts with the Hero will be referred to as Coaches. Coaches may include any person who is assisting in teaching the Hero life skills, such as parents, other family members, teachers, therapists, and other medical professionals.

Figure 1:
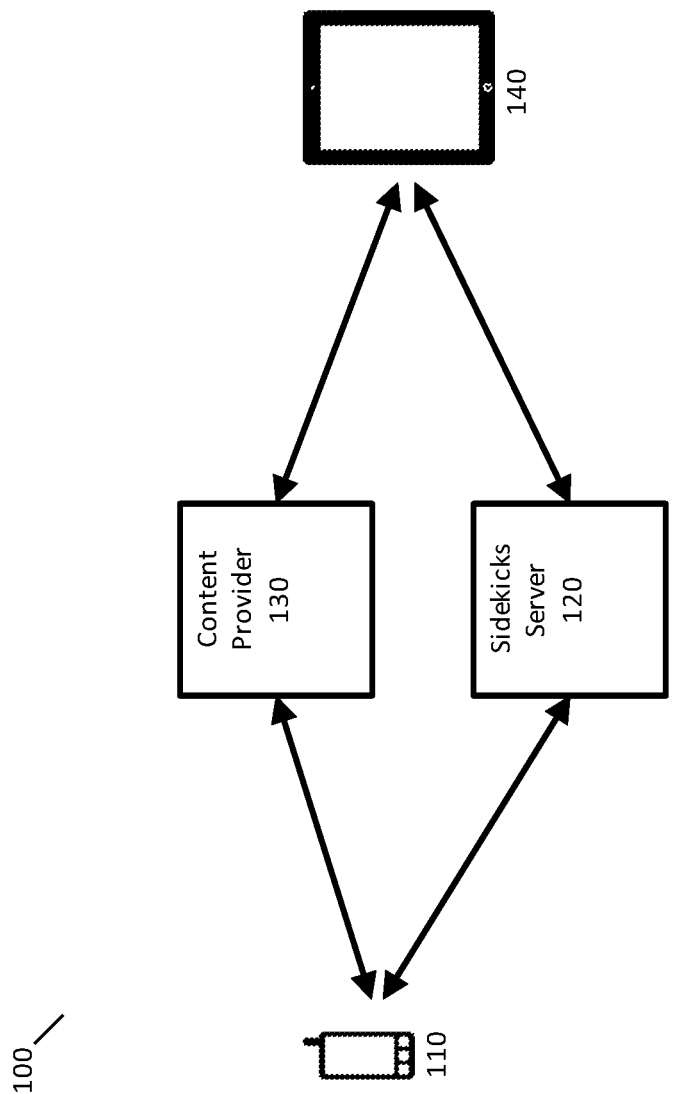
FIG. 1 illustrates a system for allowing a Coach and Hero to interact via a guided personal assistant.

FIG. 1 shows an example of a system 100 where a Coach may guide how a Sidekick interacts with the Hero. The Hero may have a Hero computing device 110, which may be a smart phone, smart watch, or any other type of computing device. The Hero device 110 may have an application that allows the Hero to interact with a Sidekick. The Coach may have a Coach computing device 140, which may be a personal computer, tablet, smart phone, or any other type of computing device. Coach device 140 may have an application that allows the Coach to guide how the Sidekick interacts with the Hero. FIG. 1 shows only one Hero and one Coach, but a single Hero may interact with multiple Coaches and vice versa.

The overall service that allows a Heroes and Coaches to interact with each other through a Sidekick will be referred to as the Sidekicks service. A company may provide the Sidekicks service that allows Heroes and Coaches to communicate as set forth in the system 100 of FIG. 1. For example, a company may provide software that can be installed on or used with a Hero Device and a Coach device (e.g., an installed application or a web page) and may also provide access to server computers that provide the functionality described herein.

For clarity in the presentation, (i) an example Hero device will be generally described as a smartphone that has a touchscreen, camera, microphone, and speakers, where the Hero interacts with the device by touching or viewing the screen, speaking into the microphone, listening to audio from a speaker, or making use of the camera; (ii) an example application on the Hero device will be generally described as a special-purpose application installed on the smartphone (such as installed from an app store); (iii) an example Coach device will be generally described as a personal computer where the Coach interacts with the device by clicking a mouse, typing on a keyboard, listening to audio from a speaker, or dictating commands; and (iv) an example application on the Coach device will be generally described as a web browser displaying a web page of the Sidekicks service. The techniques described herein are not, however, limited to these particular types of devices and applications running on the devices, and the devices need not have all of the characteristics described above. For example, that Hero device may instead be a personal computer, and the Coach device may instead be a phone or a tablet.

The Hero may open an application on Hero device 110 to begin interaction with the Sidekicks service. The application may present a graphic of a Sidekick and welcome the Hero by playing a greeting, such as "Welcome Dan!" by using a text-to-speech (TTS) voice created for the Sidekick. The Hero may speak to the Sidekick, and the Hero's voice may be captured by a microphone of Hero device 110, transmitted to the Coach device 140, and played, in real time, on speakers of the Coach device 140. In other configurations, the Hero might communicate with the Sidekick by using a keyboard or a virtual keyboard. Even when the Hero communicates using a keyboard, audio captured by a microphone of the Hero device may still be transmitted to the Coach so that the Coach can better understand the Hero's environment and mood.

The Coach may then determine an appropriate response for the Sidekick to speak. The Coach may type the response on Coach device 140. The Coach may also provide the response by speaking and using automated speech recognition to generate the response text. The text of the response may then be converted to audio using the TTS voice of the Sidekick, and the audio may be played from Hero device 110, and/or be displayed on the Hero device 110, so that it appears to the Hero that the Sidekick is automated.

System 100 may have a Sidekicks server 120 that assists with the above interactions. For example, Sidekicks server 120 may facilitate network connections between Hero device 110 and Coach device 140, may perform operations such as generating audio using the TTS voice of the Sidekick, or may perform any other operation to assist with the above interactions.

The Coach and Hero may also view and listen to content together, such as audio or video clips. The Hero device and Coach device may be synchronized so that the Hero and Coach can consume the same content simultaneously. The Hero device and the Coach device may obtain the content from Sidekicks server 120 or from another source, such as content provider 130. Content provider 130 may be any available source of content, such as YouTube or Amazon Instant Video, or a private source of content, such as a private server.

System 100 may include a variety of other interactions and features that will be described in greater detail below. Before using the Sidekick services, however, the participants may need to be registered with the service.

Registration

A company may provide the above described Sidekicks service. The company may provide a website that allows individuals to sign up and register for the service. For example, a parent may register for the service on behalf of a Hero. Since the Sidekicks service involves participation by multiple people (a Hero and at least one Coach), registration with the service may include specifying a group of people that may be referred to as a team. For example, the team may be named after the Hero, such as Team Dan. Each member of the team may have an account, such as an account for the Hero and an account for each Coach. The Hero account and Coach account may have different features and there may be different types of Coach accounts.

One step of registration may include specifying information about the Hero. This information may include any relevant information about the Hero, such as name, date of birth, gender, and a photo. Since a Sidekick will be speaking to the Hero, a phonetic pronunciation of the Hero's name may be provided to ensure that the Sidekick speaks the Hero's name correctly. An initial password for the Coach and the Hero may also be provided or generated. Personal information and preferences of the Hero may also be provided, so that a Coach can tailor his interactions to be optimized for the Hero's understanding, engagement, ability to address deficit areas, and so on.

Figure 2B:
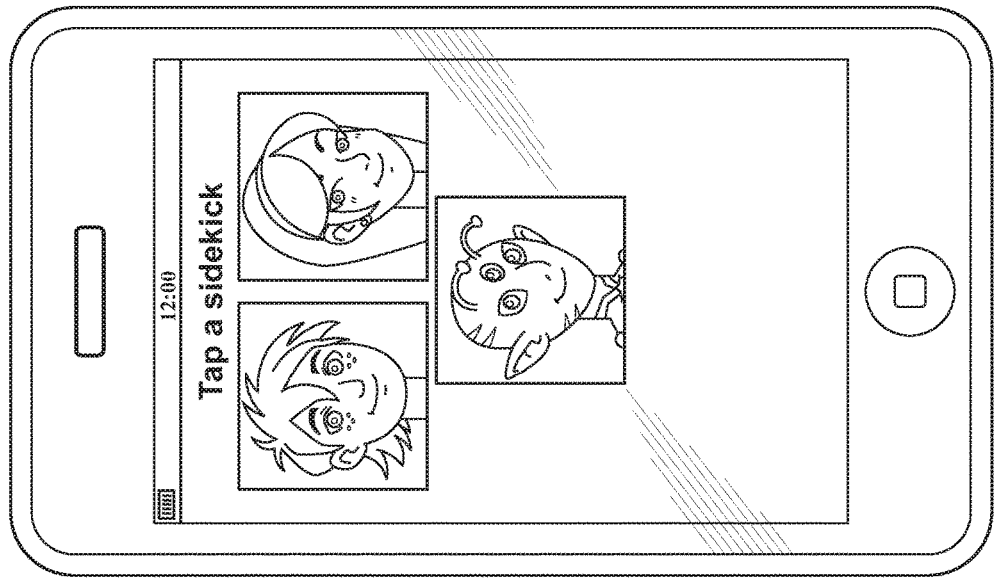
FIG. 2B illustrates an example display of a Hero device when the Coach is available.

During registration, one or more Sidekicks may be selected to be made available to the Hero on the Hero device as the Hero's designated conversational interfaces. A list of selected Sidekicks may be presented on the Hero device, for example as shown in FIG. 2B, allowing the Hero to vary his experience by choosing different Sidekicks from time to time that evince different appearances, voices, personalities, or knowledge.

As described in greater detail below, the operation of the Sidekicks service may include presenting content to the Hero based on the interests of the Hero. For example, the Hero may be interested in certain movies, such as Disney movies, Lego, or My Little Pony. Or the Hero might be especially fascinated by particular categories of items, such as dinosaurs, train schedules, or birds of Africa. The content presented to the Hero may include, for example, quotes or video clips from the movie or television interests of the Hero, or audio and video which feature his preferred categories of interests. To facilitate presenting content related to the Hero's interests, the registration process may include providing one or more interests of the Hero. In some implementations, a list of possible interests may be provided, and one or more of these interests may be selected during the registration process.

The parent registering with the Sidekick services may desire to use the Sidekicks service to improve certain life skills of the Hero. The desired improvements will be referred to herein as "goals." The particular goals that a Hero needs to develop may be based on the Hero's special needs or individual characteristics of the Hero. The registration process may allow the selection of goals for the Coaches to consider when interacting with the Hero. The goals may include categories, such as emotional, social, practical, or fun. Each category may have examples of phrases. The emotional category may include, for example, "Celebrating our differences," "Doing things you don't want to," and "Believing in yourself." The social category may include, for example, "Making friends," "Strategies for dealing with a bully," and "Introducing people to one another." The practical category may include, for example, "Bedtime routine," "Riding the bus," and "Asking for directions." The fun category may include, for example, "Enjoy a funny video clip together" and "Tell each other jokes and riddles."

During the registration process, accounts may be created for each Coach on the team. The person performing the registration may be but need not be a Coach on the team.

Different Coaches may have different roles and/or permissions. For example, one or more Coaches (likely a parent of the Hero) may be specified as an owner and/or admin of the team and may be the only person who has permissions to add or remove other Coaches to the team. When creating an account for a Coach, information such as name, email address, phone number, and a picture may be provided, as well as permissions to be granted to the Coach when participating with this team. For example, certain Coaches may be restricted to only conversing through the Sidekick on a subset of goals, or during certain times of the week, or they may be restricted from or approved for using colorful language. The person performing the registration may enter information for all Coaches or may send an invitation (e.g., by email) to Coaches to create an account. A person may be a Coach on more than one team, such as a therapist who may use the Sidekicks service with multiple clients or a parent who is a Coach for more than one child.

After the registration process is complete, the Hero and each Coach may set up their respective devices to use the Sidekicks service. The Hero and Coaches may access the Sidekicks service, for example, by using an app or going to a webpage created by the providers of the Sidekicks service. The Hero and Coaches may use different apps or webpages since the Sidekicks service may perform differently for each. The Hero and Coaches may enter a password or other authentication credentials to gain access to the service.

Initiation of Session by Coach or Hero

After the Hero and at least one Coach for that Hero have set up their devices to use the Sidekicks service, they may start using the Sidekicks service together. The use of the Sidekicks service at any particular time may be referred to as a session, and a session may be initiated by either a Coach or a Hero. Initiation by a Coach will be described first and then followed by initiation by the Hero.

A Coach may begin the process of initiating a Sidekicks session on a Coach device by, for example, opening an application or going to a particular web page to obtain an interface for initiating a Sidekicks session. In some implementations, a Coach may be part of more than one team (i.e., interact with more than one Hero) and a Coach may need to choose a Hero or team after starting the Sidekicks service. For example, a list of teams may be presented, and the Coach may select a team.

After selecting a team or if the Coach is a member of only one team, the interface may progress to the next stage. In some implementations, the next state may include the Coach setting preferences or parameters for the session, for example, as shown in FIG. 3A.

Figure 3A:
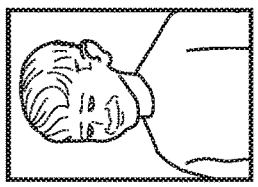
FIG. 3A illustrates an example display of a Coach device for selecting parameters for guiding a personal companion.

In the example of FIG. 3A, a Coach may select interests and goals, such as the interests and goals described above. The selected interests and goals may be used to provide suggestions to the Coach during the session. For example, as described in greater detail below, the Sidekicks service may provide suggested phrases to be spoken by the Sidekick or suggested audio or video clips to use with the Hero during a session. The presented interests and goals may be a complete list of available interests and goals or may be a subset of interests and goals that was selected during the registration process.

Using the interface of FIG. 3A, the Coach may select one or more interests of the Hero to use during the session. The interests may include, for example, movies that the Hero enjoys. A Coach may select, for example, a movie that the Hero recently watched or a movie that is relevant to the objectives of the session. In the example of FIG. 3A, the Coach has selected "Harry Potter movies" as the interest for the session.

A Coach may also select goals to focus on for the session, such as the goals shown in FIG. 3A. In some implementations, not all goals are available for all interests. After the Coach selects one or more interests, the goals list may indicate which goals are available for the selected interest. For example, unavailable goals may be grayed out or removed from the list. In FIG. 3A, for example, the display of the goal "BONDING: Bond over sad scenes together" has been modified to indicate that it is not available for the selected interest. Not all interest and goal combinations may be available because a particular interest may not be suitable for some goals or because content has not yet been created for particular interest and goal combination. In some implementations, the Coach may select one or more goals first, and in response to the selected goals, the interests list may be modified to show available interests, and interests that are not available may be grayed out or removed from the list.

After selecting parameters, such as interests or goals, the Coach may click "Done" to continue with initiating a Sidekicks session. Afterwards, the Coach may see a display similar to FIG. 3B. Where the Coach is using a device with a smaller screen, such as a phone or a tablet, the user interface may be simplified and some features may be omitted.

Figure 3B:
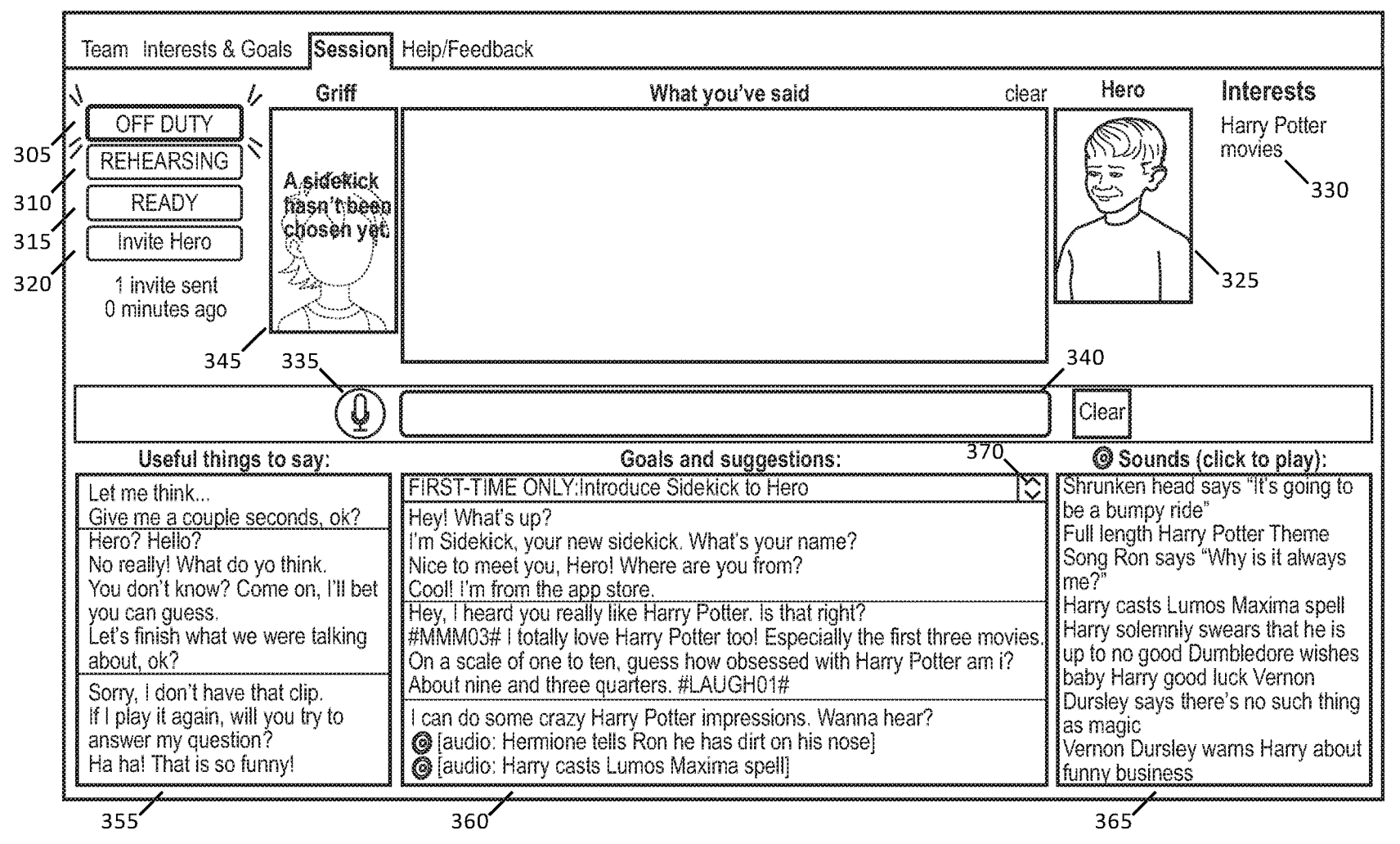

FIG. 3B shows a console that may be presented on a display of the Coach device to allow the Coach to interact with the Hero via a Sidekick. The console may have multiple states to allow a Coach to prepare for a session. For example, the console may have an "Off Duty" state, a "Rehearsing" state, and a "Ready" state. The Coach may change the state of the console, for example, by clicking the buttons 305, 310, and 315 shown in FIG. 3B. In the Off Duty state, the console may not be connected to the Hero device or any other device. In the Rehearsing state, the Coach may learn how to use the Sidekicks service or prepare for a session with the Hero. In the Ready state, the Coach may be able to communicate with the Hero via the Sidekick as described in greater detail below.

FIG. 3B shows an example of a Coach's console in the Off Duty state. In the Off Duty state, that console may show information such as a picture 325 of the Hero or the interest 330 that was selected for the session. The console may have an indication of whether the Hero has opened the Sidekick application on the Hero device and/or has selected a Sidekick. For example, the console may have a placeholder 345 for the Sidekick that indicates that a Sidekick has not been selected. In the Off Duty state, the console may show input controls such as microphone control 335 and text entry control 340, but in the Off Duty state these controls may be disabled.

The Coach may enter the Rehearsing state by clicking button 310. In the Rehearsing state, the Coach may experience both sides of a Sidekicks session simultaneously by using a second device in conjunction with the Coach device. For example, the Coach may rehearse with his own smartphone or may use the Hero device for the purpose of rehearsing. The Coach may thus be using a personal computer that displays a console similar to FIG. 3B and a smartphone that displays an interface similar to FIGS. 2A-2D. The Coach may use the console to communicate as the Sidekick and observe the results on the smartphone or vice versa. In rehearsing mode, the audio recorded by the Hero device may not be played by the Coach device to prevent feedback from the microphone of the Hero device picking up its own audio.

The console may have an Invite Hero button 320 to invite the Hero to a Sidekicks session. For example, if the Hero does not have the Sidekicks application open on his device or the application has been idle, the Coach may send an invitation to the Hero. The invitation may cause a message to be sent to the Hero, and the message may take any appropriate form, such as an operating system notification (e.g., on iOS or Android devices), a text message, or an email message. The message may inform the Hero that a Sidekick would like to speak with him. A Coach may send more than one invitation if a Hero does not respond right away.

When the Coach is ready to begin the session, the Coach may click on the Ready button 315 to put the console into the Ready state. Putting the console into the Ready state may enable input controls, such as microphone control 335 and text entry control 340. The Coach may enter the Ready state either before or after inviting the Hero by clicking the Invite Hero button 320.

In response to receiving the message, the Hero may open the Sidekicks application on the Hero device. If more than one Sidekick is available to the Hero, the Hero may see a display similar to FIG. 2B after opening the Sidekick application. The Coach console may then present a message to the Coach indicating that the Sidekicks application has been opened on the Hero device, but that the Hero has not yet selected a Sidekick. The Hero then selects a Sidekick to begin communications. After the Hero selects a Sidekick (e.g., by touching the Sidekick on the screen), the Hero may see a display similar to FIG. 2C. If only one Sidekick is available to the Hero, then the Hero may see a display similar to FIG. 2C after opening the Sidekicks app.

Figure 3C:
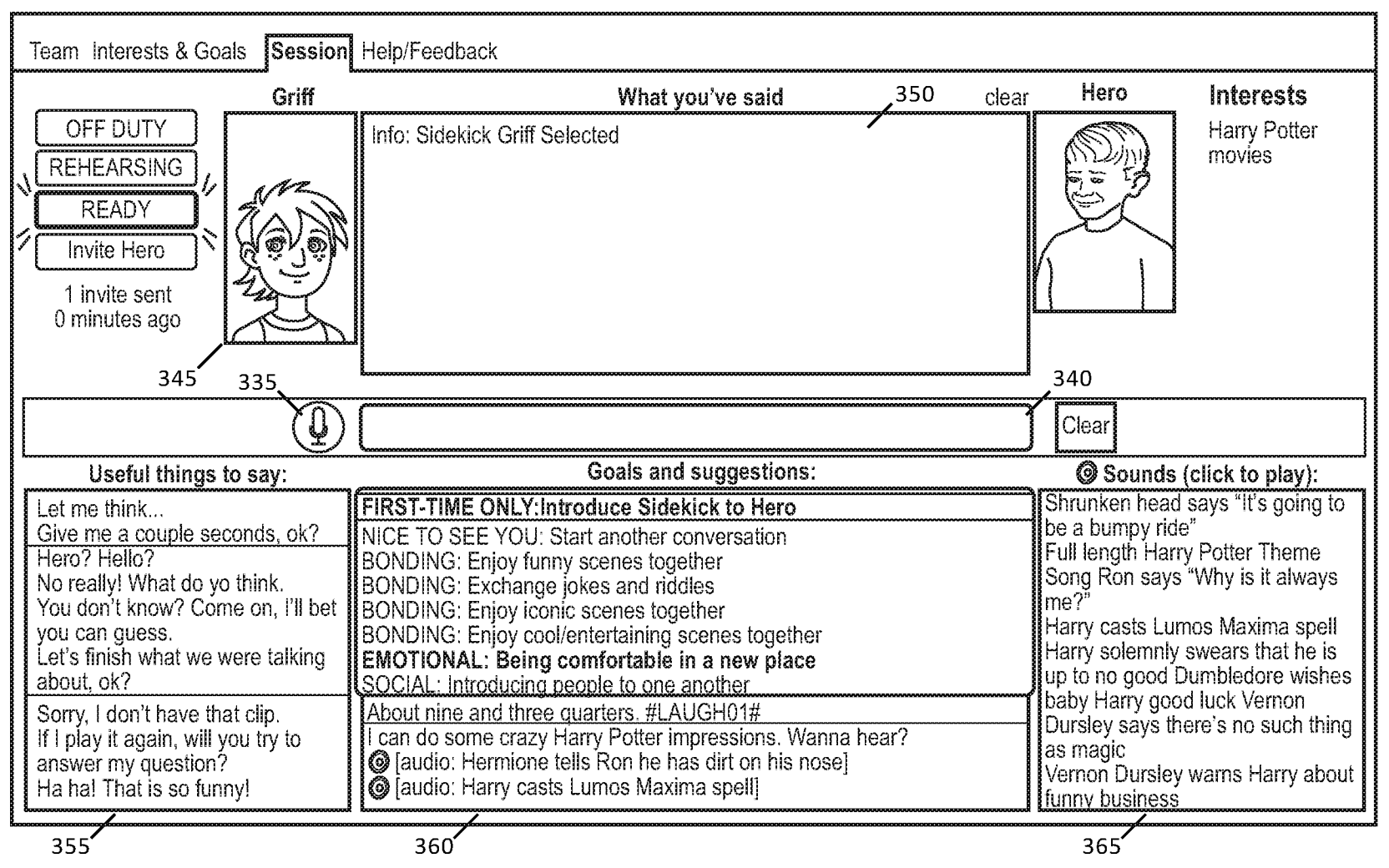

After the Hero has selected a Sidekick, the Coach device may display a console similar to FIG. 3C. In the console, the placeholder 345 for the Sidekick may be replaced by an image of the selected Sidekick as shown in FIG. 3C. The console may also have a transcript box 350 that presents a message indicating that a Sidekick was selected. With the Coach console in the Ready state and the Sidekicks application opened (and a Sidekick selected) on the Hero device, the Hero and Coach may now communicate with each other via the Sidekick as described in greater detail below.

The above sequence of steps may be modified or supplemented in a variety of ways. For example, in some implementations the selection of interests and/or goals may be performed on the same display that the Coach uses to communicate with the Hero. This may make it easier for the Coach to change the selection of interests and/or goals during a conversation. In some implementations, the selection of interests and/or goals may be presented on a different tab of a display, and the Coach may switch to a different tab during the conversation to change the selection of interests and/or goals and then go back to the tab used to communicate with the Hero.

Figure 2A:
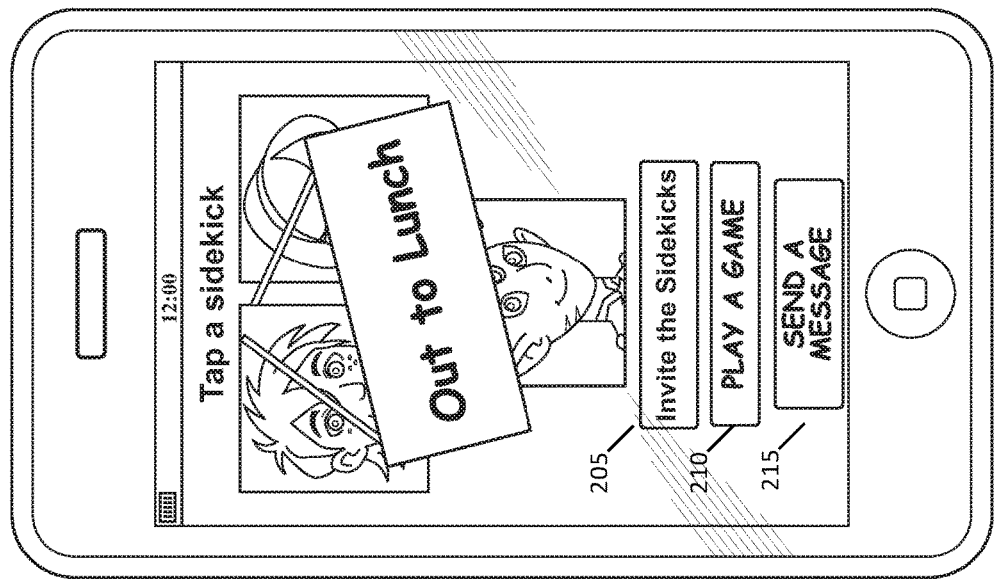
FIG. 2A illustrates an example display of a Hero device when the Coach is not available.

The above sequence of steps describes a Coach initiating a Sidekicks session, but a Hero may also initiate a Sidekicks session. The Hero may start the process of initiating a Sidekicks session by opening the Sidekicks application on the Hero device. If no Coaches are available, then the Hero may see a display similar to FIG. 2A. (If a Coach is available, then the process may proceed as described above.) Because no Coaches are available, FIG. 2A presents an indication that the Sidekicks are not available, for example, by presenting an "Out to lunch" sign or representing the Sidekicks in gray rather than in color.

The display may have an invite button 205 with text such as "Invite the Sidekicks" where the Hero can request that Sidekicks be available. When the Hero touches invite button 205, a message may be sent to one or more Coaches to inform them that the Hero is requesting to speak to a Sidekick. The message may be sent to the Coaches using any appropriate techniques, such as sending an email or text message or popping up a notification on a display of a Coach device. If none of the Coaches responds to the notification within a specified period of time (e.g., 5 minutes), then a message may be displayed on the Hero's device, such as "Sorry, no Sidekicks available right now."

If a Coach is available to guide a Sidekick, the Coach may proceed with some or all of the steps described above. If the Coach does not have the Sidekicks website open, the Coach may go to the Coach website and sign in. Alternatively, the Coach may already have the Sidekicks website open but may not be in the Ready State, or the Coach may be communicating with a different Hero. If the Coach is able to communicate with the requesting Hero, the Coach may select goals and interests for the session, may rehearse, and may click the "Ready" button to begin communications with the requesting Hero via the Sidekick. In response to the Coach clicking the Ready button, a message may be sent to the Hero device and the display of the Hero's device may change to indicate that Sidekicks are available, such as the display of FIG. 2B. For example, the out to lunch sign may be removed, the Sidekicks may change from gray to color, or a notification sound may play. The Hero may then select a Sidekick, and the Hero and Coach may then communicate via the Sidekick as described in greater detail below.

The Hero device may display other options when Coaches are not available. In some implementations, as shown in FIG. 2A, the Hero may click a Send Message button 215 to send a message to a Sidekick that will be received by a Coach at a later time. For example, the Hero could type or speak a message and this message could be placed into the inboxes of the Coaches (e.g., an email inbox or an inbox in the Sidekicks service). The Sidekicks app on the Hero device may also have other options to engage the Hero when the Coaches are not available. For example, the display may have buttons to allow the Hero to play a game (e.g., via Play a Game button 210), to view some of the Hero's favorite video clips, or to review past conversations with Sidekicks.

Communications in a Session

Additional details are now presented regarding the communications in a Sidekick session. One aspect of a Sidekick session comprises the Hero communicating with the Sidekick on the Hero device using speech and/or text. For example, if the Hero is by himself, he may prefer to speak, but if others are present, he may prefer to type text. The Coach is able to hear the Hero speaking to the Sidekick and/or see the text typed by the Hero. The Coach may then cause the Sidekick to respond to the Hero. Either the Hero or Sidekick may start the conversation. In some implementations, the Hero may communicate by speaking and the Sidekick may communicate by text or vice versa.

The Hero may speak to the Sidekick by speaking into a microphone of the Hero device. This audio may be transmitted to the Coach device in real time so that the Coach can hear the speech of the Hero in real time. The Hero may also communicate with the Sidekick by typing text on the Hero device, and this text may be presented on the Coach's console. In some implementations, the typing of the Hero may be transmitted to the Coach's console in real time so that the Coach sees each letter as it is typed and sees corrections to the text made by the Hero.

Figure 3D:
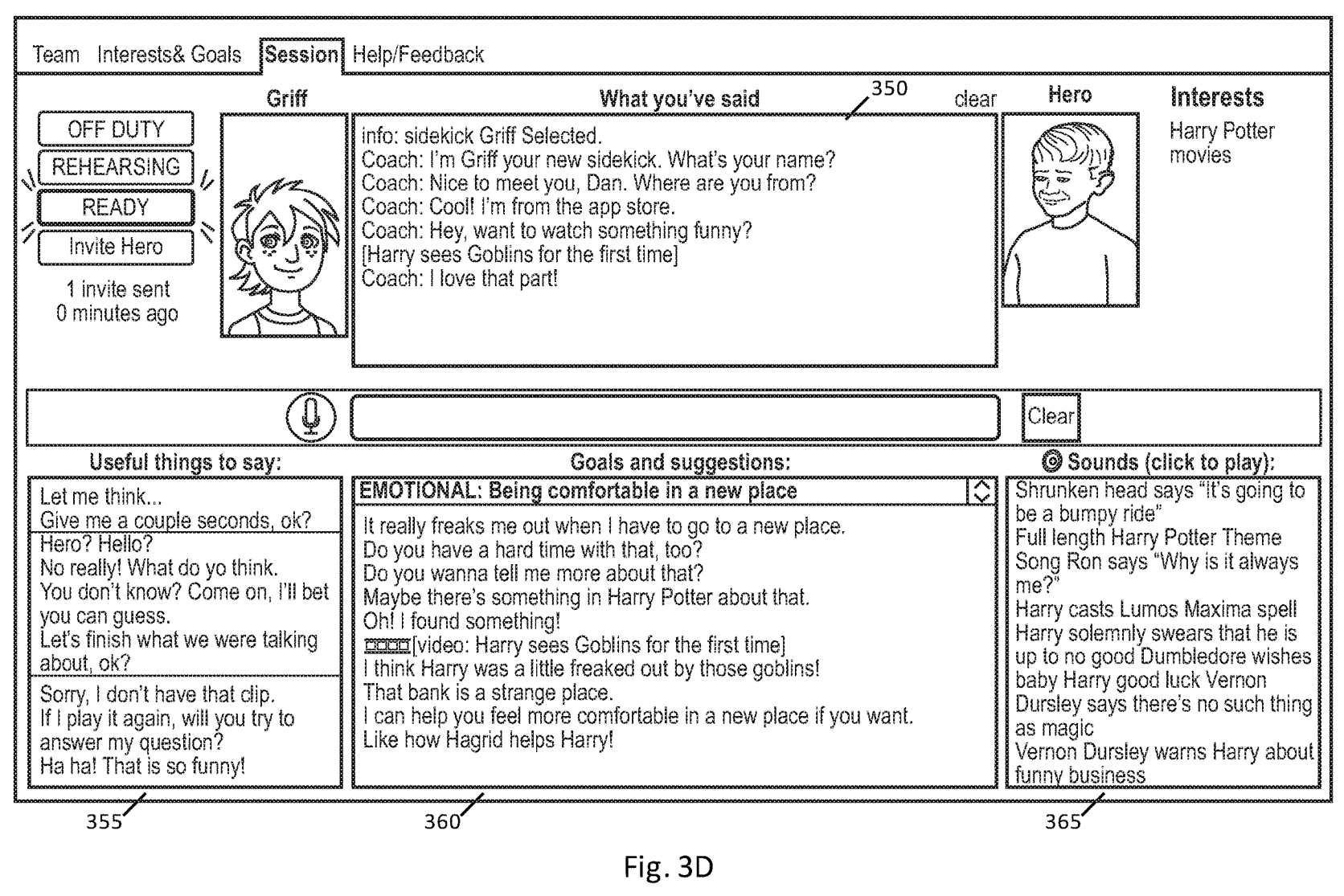

The Coach may cause the Sidekick to respond using the Coach's console, such as the console of FIGS. 3C and 3D. The Coach may cause the Sidekick to respond by typing text into text entry control 340. After typing the text, the Coach may send the text by pressing an enter key or clicking a send button on the console. If the Sidekick is communicating to the Hero by speaking, then the text may be converted to audio by using a text-to-speech voice of the Sidekick and then causing the Hero device to play the audio on a speaker of the Hero device. If the Sidekick is communicating to the Hero by text, then the text typed by the Coach may appear on the display of the Hero device. Whether the Sidekick is communicating by speaking or text may be an option selected by the Hero, an option selected by the Coach, or it may match how the Hero is communicating to the Sidekick (e.g., if the Hero speaks to the Sidekick, then the Sidekick will speak back to the Hero). In some implementations, the Sidekick may communicate to the Hero using both audio and text simultaneously.

The Coach may also use speech recognition to assist in generating text for the Sidekick's response to the Hero. The Coach may use microphone control 335 to start and stop recording his speech, and speech recognition may be used to display the text of the Coach's speech in the text entry control 340. The Coach may then send the text or edit it before sending. As above, the Sidekick may then speak the text and/or the text may appear on the Hero device. In some implementations, a key on the keyboard may be used to cause the microphone of the Coach device to start and stop recording. For example, a "tab" key may be used for this purpose. The Coach may then mix speaking and typing in formulating responses by using only the keyboard to control composition of the response.

Figure 2C:
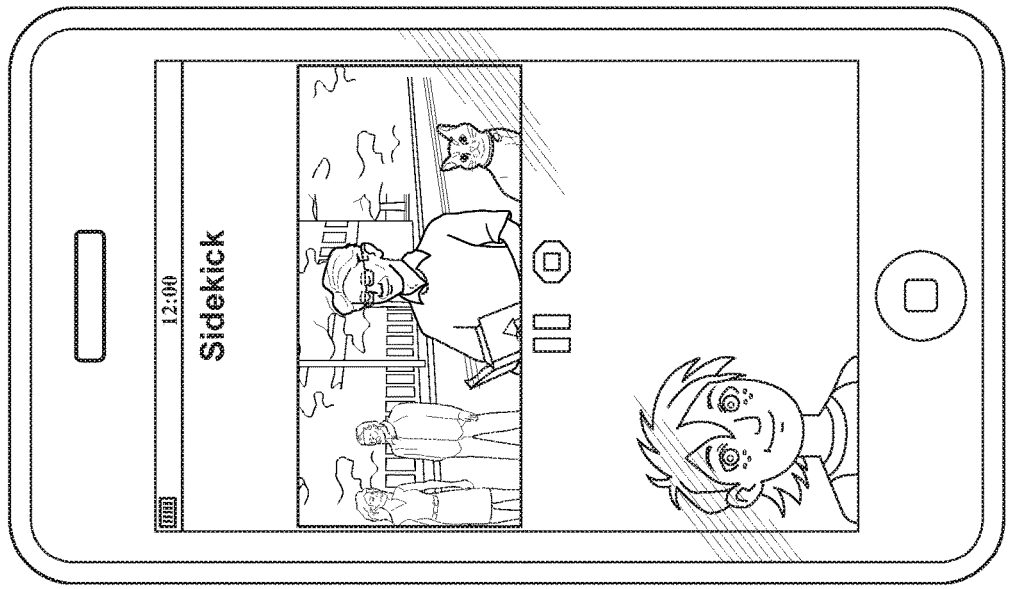
FIG. 2C illustrates an example display of a Hero device with a transcript of a session.

One or both of the Hero device and the Coach device may show a transcript of the session. The transcript may include just the Hero side of the conversation (words spoken by or typed by the Hero), just the Sidekick side of the conversation (words spoken by the Sidekick or typed by the Coach for the sidekick), or both sides of the conversation. The transcript may appear, for example, in Hero device transcript box 220 in FIG. 2C or the Coach device transcript box 350 in FIG. 3D (the examples of FIGS. 2C and 3D show just the Sidekick side of the conversation). Where the Hero is speaking to the Sidekick, speech recognition may be used to convert the Hero's speech to text, and this transcribed text may be included in the transcript. The transcript may be saved for later review and analysis as described in greater detail below.

In some implementations, the Coach may click on an item (e.g., words previously communicated by the Hero or Sidekick) in the Coach device transcript box 350 to cause that item to be copied into text entry control 340. The Coach may want to reuse the item or may want to edit it before sending (e.g., to fix a mistake in a previous communication). In some implementations, the Coach may be able to remove an item from the transcript, for example, if the Coach made a mistake. Removing an item from the transcript, may remove the corresponding text from the display of the Hero device (e.g., from Hero device transcript box 220) and may stop the Sidekick from speaking the item if that Sidekick has not finished speaking the item.

One aspect of the Coach's console is to assist the Coach in communicating with the Hero. For example, some parents may need assistance with how they can best interact with their special needs children using Sidekicks. The console may provide both suggestions and shortcuts to speed up the process of causing a Sidekick to communicate. It may be faster for a Coach to select a suggested phrase rather than thinking about an appropriate response and then typing or speaking the response prior to sending. The Sidekicks service may provide suggestions to a Coach in a variety of ways, and the Sidekicks service is not limited to the following examples.

The Coach's console may present a list of common phrases to be spoken by the Sidekick, such as the "Useful things to say" box 355 in FIG. 3B. For example, it may arise frequently that a Coach needs to think about how to formulate a response, and the Coach may send a filler response, such as "Let me think . . . " or "Give me a couple seconds, ok?" The "Useful things to say" box provides other examples of potentially common phrases. These phrases may be provided by the Sidekicks service, may be specified by a Coach, parent, or admin, or may be automatically learned (e.g., presenting the top 10 phrases previously spoken by a Sidekick).

The Coach's console may present a list of phrases relating to parameters specified by the Coach, such as the selected interests and goals discussed above. In some implementations, the suggested phrases may be grouped into different categories and the Coach may switch between the different categories to show phrases corresponding to a selected category. In the example of FIGS. 3B, 3C, and 3D, the categories are the previously selected goals, and the console provides a list of phrases for each of the previously selected goals. Any appropriate user interface elements may be used to allow the Coach to switch between different categories of phrases.

In the example of FIG. 3B, the goals and suggestions box 360 shows a drop-down menu on the first line. The selected item of the drop-down menu is the goal "FIRST-TIME ONLY: Introduce Sidekick to Hero." The Coach may select a different goal using the control 370 of the drop-down menu. Activating the control 370 shows the other categories in the drop-down menu, such as the categories displayed in the goals and suggestions box 360 in FIG. 3C. The other goals available to be selected include "EMOTIONAL: Being comfortable in a new place" and "SOCIAL: Introducing people to one another." FIG. 3D shows the goals and suggestions box 360 after the coach has selected the goal "EMOTIONAL: Being comfortable in a new place." Accordingly, the suggested phrases in the goals and suggestions box 360 of FIG. 3B relate to the goal "FIRST-TIME ONLY: Introduce Sidekick to Hero" and the suggested phrases in the goals and suggestions box 360 of FIG. 3D relate to the goal "EMOTIONAL: Being comfortable in a new place."

A Coach may use the suggested phrases during a session. For example, clicking on a suggested phrase may copy the phrase to the text entry control 340, and the Coach may send the phrase as is or edit it before sending. A Coach may mix suggested phrases with his own phrases as needed. For example, a Coach may use a suggested phrase and receive a response from the Hero. None of the suggested phrases may be a suitable response to the Hero so the Coach may type an appropriate response in the text box.

A Coach may change the goal during the session. For example, after introducing the Hero to the Sidekick, the Coach may want to change the goal to "EMOTIONAL: Being comfortable in a new place." After changing the goal, the new list of suggested phrases will appear as shown in FIG. 3D. The Coach may then cause the Sidekick to say things to work on the goal, either by using the suggested phrases or creating his own phrases.

Figure 2D:
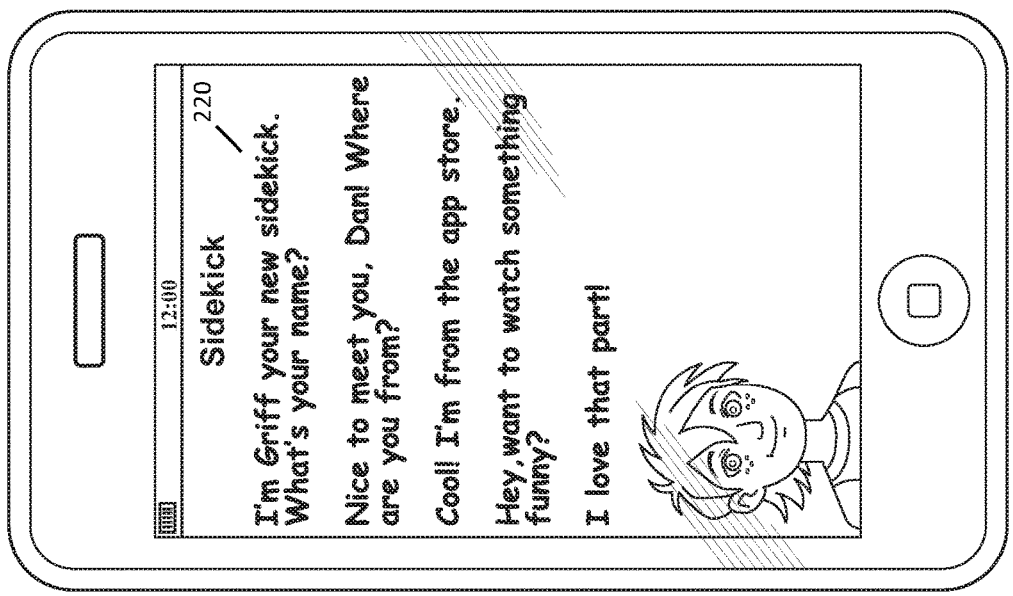
FIG. 2D illustrates an example display of a Hero device with a video playing.

The suggestions provided by the Sidekicks service may include video clips, such as video clips relating to the interests of the Hero. For example, in FIG. 3D, a video clip is included in goals and suggestions box 360 that relates to the goal of introducing people to one another. This video may be indicated by a special icon and may have text with a short description of the video (e.g., "Video: Harry sees Goblins for the first time"). The Coach may select a video clip to cause the video clip to be played on the Hero's device. FIG. 2D illustrates an example of playing a video clip on the Hero device where the video is presented on top of the transcript. In some implementations, either one or both of the Hero and the Coach may be able to control the playing of the video clip by using controls that allow operations such as playing, pausing, resuming, or scrubbing. The Coach may cause the Sidekick to introduce the video clip and ask questions of the Hero during or after the video clip.

In some implementations, the video clip may also be presented on the display of the Coach device, and the presentation on the Coach device may be in sync with the presentation on the Hero device. Because the Coach may be able to hear a live stream of audio from the Hero device, the Coach device may not play the audio of the video clip since the Coach will hear the audio of the video clip from the Hero device.

Any appropriate techniques may be used to synchronize the presentation of the video on the Hero and Coach devices. In some implementations, each of the Hero and Coach devices may obtain a video stream from a server (such as content provider 130 of FIG. 1), and at least one of the Hero or Coach device may send time stamps to the other to keep the videos in sync. In some implementations, the Hero device may transmit the video clip or portions of it to the Coach device. To reduce bandwidth, the Hero device may send a subset of the video frames to the Coach device, such as one frame per second, and/or compress the video frames. The frame rate and compression rate may be determined based on network bandwidth between the Hero device and the Coach device and may be modified dynamically during a video presentation. In some implementations, the frame of the video may be captured from the display of the Hero device and transmitted to the Coach device.

The Coach's console may also have a list of sounds that the Coach can cause to be played on the Hero's device, such as the list of sounds in the sounds box 365 in FIG. 3C. The Coach may click on the sound to cause it to be played. The sounds may relate to the goal, may be for regaining the attention of the Hero, or may simply be for fun.

The above examples of suggested phrases, video clips, and sounds, are a few examples of how the Sidekicks service may provide suggestions to a Coach, but the suggestions provided by the Sidekicks service are not limited by these examples and any appropriate suggestions may be given.

In some implementations, the Coach's console may provide additional guidance to a Coach, such as an outline of a suggested session plan with multiple steps to be used with the Hero. For example, the Coach's console may present a "Session plan" with a higher level outline of a session with steps, such as (1) Exchange "How are you's", (2) Jokes & fun, (3) Introduce "hugging" goal, (4) Play one or more scenes, (5) Prompt a follow-up discussion, and (6) Say goodbye. The session plan may be created by the Coach or by other people. For example, a Coach could create the session plan before starting the session or the session plan could be created by a therapist to be used by a parent acting as the Coach.

In some implementations, the Coach may be able to click the steps of the session plan to tailor the presented phrases to the current session plan step. When the Coach starts the session, the first step of the session plan may be initially highlighted and the phrases in other boxes (such as goals and suggestion box 360) may relate to that step of the session plan. When the Coach is ready to proceed to the next step of the session plan, the Coach may select the next step (e.g., by clicking with a mouse) and the phrases in the other boxes may be updated to correspond to the next step of the session plan. In this manner, a Coach may progress through the steps of the session plan and have easy access to suggested phrases relating to that step of the session plan. If the conversation progresses back to a previous step of the session plan, the Coach may go back and select a previous step to again obtain phrases relating to that step. Alternatively, the Coach may skip a step of the session plan or end the session early depending on the effectiveness of the conversation with the Hero.

In some implementations, multiple Coaches may participate simultaneously when interacting with a Hero. Any appropriate techniques may be used to allow Coaches to work together. In some implementations, each Coach will have his own Coach computer for viewing the Coach's console. Each Coach may be able to hear and/or see the communications of the Hero and see information about other Coaches who are present. In some implementations, each Coach may be able to cause the Sidekick to speak or present text and the actions by all the participating Coaches will be implemented sequentially. In some implementations, all Coaches may view, but only one Coach, a controlling Coach, may be able to cause the Sidekick to speak or type text. The controlling Coach may be able to pass control to another Coach to have that next Coach be the controlling Coach.

Monitoring of the Hero During a Session

The Coach's console may provide additional information about the Hero so that the Coach can better understand the precise environment of the Hero and use this information to provide more suitable responses to the Hero.

In some implementations, a Coach may be able to hear all the audio from the microphone of the Hero device as soon as the Hero starts the Sidekick application. The Coach may thus be able to hear the speech of the Hero even when the Hero is not specifically talking to a Sidekick. The Coach may also hear other noises, such as the speech of people near the Hero, traffic noise, wind noise, and the like.

In some implementations, one or more cameras of the Hero device may be turned on as soon as the Hero starts the Sidekick application. If the Hero device has a front facing camera, the Coach will be able to see the Hero as soon as the Sidekicks application is started. If the Hero device has a rear facing camera, then the Coach may also be able to see the environment of the Hero and people near the Hero. The live video from cameras of the Hero device may be presented on the Coach's console. The transmission of video from from the Hero device to the Coach device may be an option that is selectable by the Coach. For example, if bandwidth is limited, the video quality or frame rate may be reduced or the Coach may choose to turn off video transmission.

In some implementations, the Hero device will transmit its location (e.g., acquired via a GPS sensor, Wi-Fi signals, or cell phone tower triangulation) to the Sidekicks service and this location may be presented on the Coach's console.

For example, a map may be shown on the Coach's console with the location of the Hero during the session.

In some implementations, the Hero device may have a galvanic skin response sensor and/or a heartbeat sensor, and this information may be transmitted to the Coach's console. The information from the galvanic skin response sensor and heartbeat sensors may aid the Coach in understanding the emotional state of the Hero.

In some implementations, the Hero device may transmit information from motion and/or orientation sensors to the Coach's console. For example, if the Hero is moving at 35 miles per hour, then the Coach can deduce that the Hero is likely on a bus or in a car. From the position of the Hero device, a Coach may be able to deduce if the Hero is standing or lying down.

Information from any other sensors of the Hero device may also be presented on the Coach's console and/or stored for future analysis, and the Sidekicks service is not limited to the foregoing examples.

Session Logging and Reviewing

In some implementations, aspects of the communications during the session may be logged and/or stored so that they may be reviewed at a later time. Information that may be stored includes any of the following: invitations from the Coach or Hero, interests and goals selected by the Coach, Sidekicks selected by the Hero, audio transmitted from the Hero device, text typed by the Hero, video of the Hero transmitted by the Hero device, audio played by the Hero device (e.g., the Sidekick speaking or audio or video clips played during the session), audio recorded or converted to text at the Coach device, text transmitted by the Coach (whether typed or selected), or an identity of audio or video clips played during the session. Information from outside of connected sessions may be stored as well, such as when the Hero plays a game and the score of the game.

In some implementations, timestamps may be stored as well. Timestamps that may be stored include any of the following: time of opening and/or closing of the Sidekicks application on the Hero device; the start and/or stop of recording audio and/or video on the Hero device; the start and/or stop of portions (e.g., phrases or words) of audio spoken by the Hero; timing of typing by the Hero (e.g., a time of sending a message or for each letter typed); a time that an instruction was received by a hero device to cause the Sidekick to speak a phrase; the start and/or stop of the playing of audio spoken by the Sidekick; the start and/or stop of playing audio and/or video clips on the Hero device (including pausing, resuming, scrubbing, etc.); or the start and/or stop of the Hero playing a game. Similar timestamps may also be stored for actions performed by the Coach on the Coach device, such as timestamps of the Coach's speaking or typing.

The stored information and timestamps may be used to recreate the session for later review or for later reuse. The Coach's console of the Sidekicks service may include a display that lists information about previous sessions and allows the Coach to review the previous sessions. For example, a list of sessions may be presented to the Coach with summary information, such as the date, time, and/or duration of the session. The Coach may select a session to review the details of the session or to reuse the Coach's side of the conversation recorded in the transcript. For example, the Coach may be able to review a text transcript of the session, play portions of stored audio of the session, or replay the session as experienced by the Hero.

The Coach may also be able to store notes relating to the session. For example, the Coach may write notes to indicate what aspects of the session were effective or not effective or to provide suggestions of goals to address for the next session.

Illustrative Processes

Figure 4:
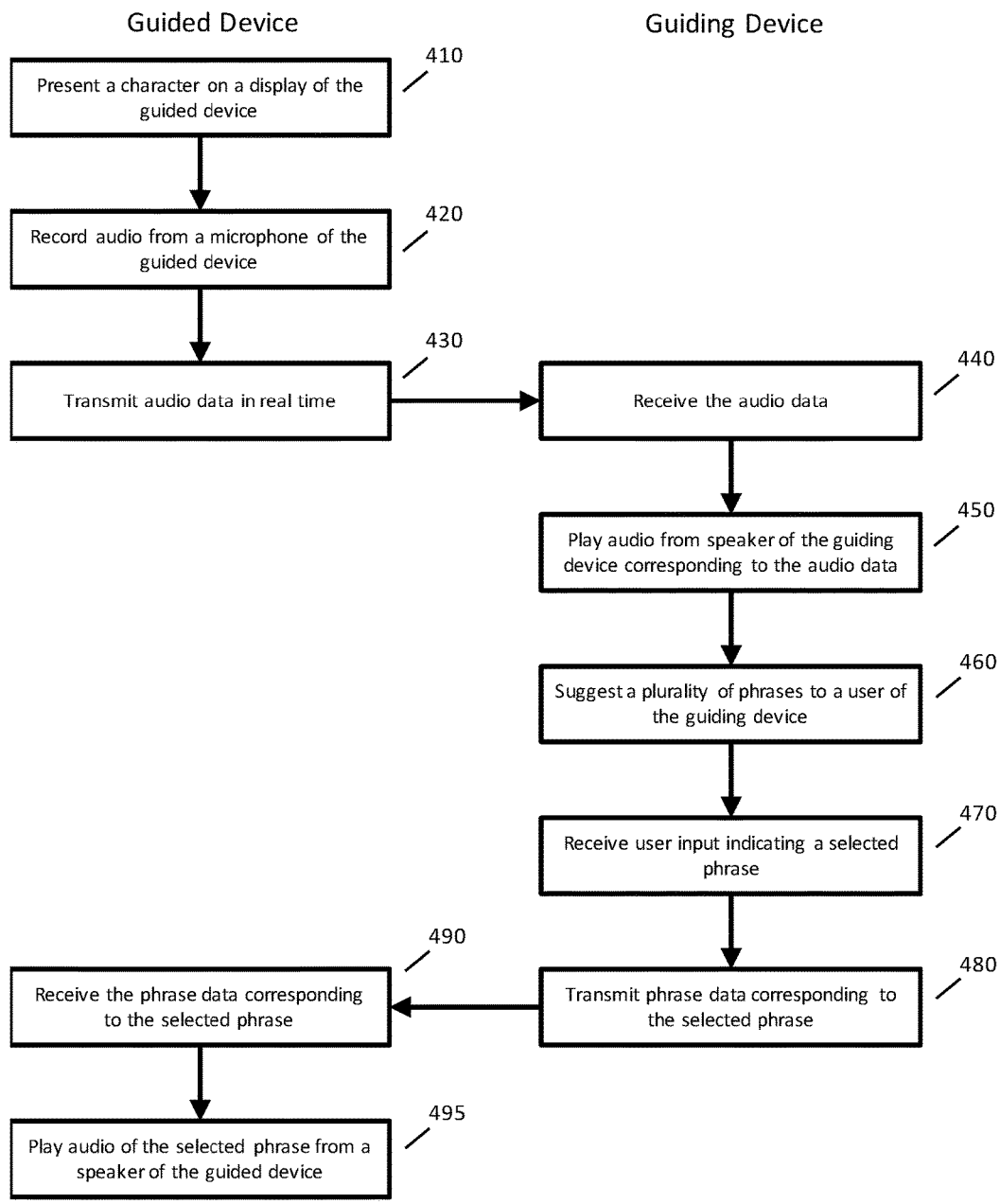
FIG. 4 is a flowchart showing an example implementation of guiding a personal companion.

In some implementations, a Coach may use a guiding device (such as a Coach device as described above) to guide a guided device used by a Hero (such as a Hero device described above) as illustrated by FIG. 4. A guiding device may be any device used by a Coach, such as any of the devices described above, to assist in guiding a Sidekick communicating with the Hero. A guided device may be any device used by a Hero, such as any of the devices described above, to interact with a Sidekick.

At step 410, a character is presented on a display of a guided device, such as by presenting an image or video of a character. A character may represent any persona or personal companion for interacting with a Hero, and a Sidekick is an example of a character. The guided device may be running any appropriate software to present the character. For example, the guided device may be running a special purpose application (or app) or may be presenting the character on a web page in a web browser of the guided device. The character may have some or all of the qualities of the Sidekick described above. The character may be a still image or may be animated, may correspond to a real person, may be a known character from a fictional work, or may be a character that was specially created for the guided device. The character may be one of several characters available to be used on the guided device and may have been selected by a user of the guided device. The user of the guided device may be a Hero as described above. The guided device may be any device that is capable of presenting a character, including but not limited to mobile devices (e.g., a smart phone), wearable devices (e.g., smart watch or glasses), and personal computers (e.g., a laptop or a desktop computer). In some implementations, the guided device need not have a display, and the character may be presented using other technologies, such as by projecting an image on a surface or presenting the character aurally.

In some implementations, a request for communications may be made by a user of the guided device or a user of the guiding device, and this request may be made before, during, or after presenting the character on the display of the guided device. For example, a user of the guided device may touch a button to transmit a request to speak with the character or a user of the guiding device may click a button to transmit a request to communicate with a user of the guided device. This request may be received by a server computer, and the server computer may send a message to the appropriate person using any of the techniques described above.

At step 420, audio is recorded or transmitted from a microphone of the guided device. The guided device may commence recording and/or transmitting audio based on a variety of criteria, including but not limited to the following: when the guided device is turned on, when an application on the guided device is opened (or the user goes to the web page that presents the character), when the user selects a character on the guided device, in response to a user selecting a control to begin recording, in response to detecting audio or speech, or in response to the user speaking a "wake word" that activates recording (such as a name of the character). The guided device may stop recording and/or transmitting audio based on a variety of criteria, including but not limited to the following: when the guided device is turned off, when an application on the guided device is closed (or the user leaves the web page that presents the character), when the user deselects a character on the guided device, in response to a user selecting a control to stop recording and/or transmitting, in response to not detecting audio or speech for at least a specified amount of time, or in response to the user speaking a command that stops recording and/or transmitting. The recorded or transmitted audio may include speech of the user of the guided device and may also include other sounds in the environment, such as nearby people, or background noise (traffic, etc.). In some implementations, the microphone need not be a microphone of the guided device or physically attached to the guided device, and the audio may be recorded or transmitted from a microphone that is proximate to the guided device.

At step 430, audio data is transmitted in real time to one or more guiding devices. The audio data may be transmitted directly to the guiding device or may be transferred via one or more server computers that facilitate communications between the guided device and the guiding device. The guided device may process the audio data before transmitting, for example, by performing end pointing, noise reduction, compression, or encoding. In some implementations, the guided device or a server computer may perform speech recognition on the audio data to obtain a transcript of the audio data.

At step 440, a guiding device receives the audio data. The guiding device may receive the audio data directly from the guided device or via one or more server computers that facilitate communication between the guided device and the guiding device. In some implementations, the audio data may be modified by a server computer during transit. For example, a server computer may perform compression or encoding of the audio data.

At step 450, the guiding device plays audio from a speaker of the guiding device corresponding to the audio data. Accordingly, a user of the guiding device may be able to hear in real time the speech of the user of the guided device and other sounds proximate to the guided device. In some implementations, the speaker need not be a speaker of the guiding device or physically attached to the guiding device, and the audio may be played from a speaker that is proximate to the guiding device.

At step 460, a plurality of phrases is suggested to a user of the guiding device. For example, the plurality of phrases may be presented on a display of the guiding device. The plurality of phrases may be presented using any appropriate software. For example, the guiding device may be running a special purpose application (or app) or may be presenting the plurality of phrases on a web page in a web browser of the guiding device. The user of the guiding device may be a Coach, as described above. The guiding device may be any device that is capable of presenting a plurality of phrases, including but not limited to mobile devices (e.g., a smart phone), wearable devices (e.g., smart watch or glasses), and personal computers (e.g., a laptop or a desktop computer). In some implementations, the guiding device need not have a display, and the plurality of phrases may be presented using other technologies, such as by projecting an image on a surface or presenting the plurality of phrases aurally. The plurality of phrases may correspond to any of the phrases described above, including but not limited to the phrases presented in the useful things to say box, the goals and suggestions box, or the sounds box.

In some implementations, the plurality of phrases is determined by a server computer and transmitted to the guiding device. In some implementations, the plurality of phrases is determined by preferences that have previously been specified, such as goals or interests as described above. In some implementations, a user of the guiding device may specify the preferences, such as during a registration process, before a communication session, or during a communication session. In some implementations, a user of the guiding device may change the preferences during a communications session, and the plurality of phrases presented on the guiding device may change in response to the change in preferences. In some implementations, a single phrase may be suggested instead of a plurality of phrases.

At step 470, user input indicating a selected phrase is received. The user input may be received using any appropriate input technology, including but not limited to recording and transcribing speech of the user, receiving keyboard input, or receiving a selection of a phrase presented on a display of the guiding device (e.g., by clicking with a mouse or touching a touch screen). The selected phrase may be the same as one of the plurality of phrases, may be modified version of one of the plurality of phrases, or may be different from all of the plurality of phrases.

At step 480, phrase data corresponding to the selected phrase is transmitted to the guided device. The phrase data may correspond to any representation of the selected phrase, such as text, input for a text-to-speech (TTS) engine, an audio representation of the selected phrase (either previously recorded or generated with a TTS engine), or an address indicating where other data may be obtained (e.g., a URL of a REST service that provides audio data). The phrase data may be transmitted directly to the guided device or may be transferred via one or more server computers that facilitate communication between the guided device and the guiding device. The guiding device may generate the phrase data before transmitting, for example, by generating audio of the selected phrase using a TTS engine.

At step 490, the guided device receives the phrase data. The guided device may receive the phrase data directly from the guiding device or via one or more server computers that facilitate communication between the guided device and the guiding device. In some implementations, the phrase data may be modified by a server computer during transit. For example, a server computer may receive phrase data in the form of an input for a TTS engine, generate audio using the received phrase data and a TTS engine, and transmit the generated audio as phrase data to the guided device.

At step 495, the guided device plays audio of the selected phrase from a speaker of the guided device. The guided device may generate the audio using any appropriate techniques, such as playing a received audio signal, generating an audio signal using a TTS engine, or obtaining an audio signal from another source (e.g., a server using a REST interface). The audio played from the speaker may correspond to a voice of the character. For example, the audio signal may have been generated (either by the guiding device, the server, or the guided device) using a TTS voice that represents desired vocal characteristics of the character. In some implementations, the character may be animated while the audio is being played. For example, the character's mouth may move, the character's face may have different facial expressions, or some elements of the image may move. In some implementations, the speaker need not be a speaker of the guided device or physically attached to the guided device, and the audio may be played from a speaker that is proximate to the guided device.

In some implementations, some or all of the communications with the guided device may be via text instead of speech. For example, at steps 420 and 430, text input may be received from a user of the guided device, and text data may be transmitted to the guiding device. At step 450, the text data may be presented on a display of the guiding device. At step 495, the guided device may present text of the selected phrase instead of playing audio of the selected phrase.

In some implementations, the operation of an application on a device may be guided as described in, among others, the following clauses and combinations of any two or more of them.

1. A system for guiding the operation of an application on a first device, the system comprising a first device and a second device, wherein:

the application on the first device is configured to:

present a character on a display of the first device, wherein the character is associated with a text-to-speech voice, obtain an audio signal from a microphone of the first device, wherein the audio signal comprises speech of a user of the first device, and transmit audio data to the second device in real time, wherein the audio data is generated from the audio signal;

the second device is configured to:

receive the audio data from the first device, cause audio to be played using the audio data, present a plurality of phrases as suggestions of phrases to be spoken by the character, receive an input from a user of the second device that specifies a selected phrase to be spoken by the character, and cause phrase data to be transmitted to the first device corresponding to the selected phrase; and the application on the first device is configured to:

receive the phrase data corresponding to the selected phrase, and cause audio to be played from the first device corresponding to the selected phrase, wherein the audio is generated using the text-to-speech voice of the character.

2. The system of clause 1, wherein:

the user of the second device is a parent or caretaker of the user of the first device; and the user of the second device selects the selected phrase to assist the user of the first device.

3. The system of clause 1, wherein the plurality of phrases comprises the selected phrase.

4. The system of clause 1, wherein the input from the user of the second device corresponds to receiving keyboard input or receiving an audio signal from a microphone connected to the second device.

5. The system of clause 1, wherein the input from the user of the second device comprises selecting a first phrase of the plurality of phrases and editing the first phrase to generate the selected phrase.

6. The system of clause 1, wherein:

the application on the first device is configured to transmit video data of the user of the first device to the second device in real time, wherein the video data is generated from a camera of the first device; and the second device is configured to receive the video data from the first device and present video on a display using the video data.

7. The system of clause 1, wherein:

the second device is configured to:

receive an input from the user of the second device corresponding to an instruction to play an audio or video clip on the first device, and send an instruction to the first device to play the audio or video clip; and the first device is configured to:

receive the instruction to play the audio or video clip, and cause the audio or video clip to be presented by the first device.

8. The system of clause 1, wherein the system comprises a server computer and wherein the application on the first device is configured to transmit the audio data to the second device in real time by transmitting the audio data via the server computer, and wherein the server computer is configured to transmit the audio data to the second device.

9. The system of clause 8, wherein the server computer is configured to:

receive preferences for communications with the user of the first device;

obtain the plurality of phrases using the preferences; and transmit the plurality of phrases to the second device.

10. The system of clause 8, wherein the server computer is configured to:

receive a request from the first device to initiate a communications session; and send a message to the user of the second device.

11. The system of clause 8, wherein the server computer is configured to:

receive a request from the second device to initiate a communications session; and send a message to the user of the first device.

12. A method for guiding the operation of an application on a first device, the method comprising:

receiving, from a second device, first preferences for communicating with the first device;

determining a first plurality of phrases using the first preferences, wherein the first plurality of phrases comprises suggestions for phrases to be spoken by a character presented on the first device;

transmitting the first plurality of phrases to the second device;

receiving, from the first device, a stream of audio data, the stream of audio data comprising speech of a user of the first device;

transmitting the stream of audio data to the second device;

receiving, from the second device, phrase data corresponding to a selected phrase;

transmitting the phrase data to the first device, wherein the phrase data enables the first device to present audio of the selected phrase;

receiving, from the second device, second preferences for communicating with the first device;

determining a second plurality of phrases using the second preferences, wherein the second plurality of phrases comprises suggestions for phrases to be spoken by the character presented on the first device; and transmitting the second plurality of phrases to the second device.

13. The method of clause 12, wherein the first preferences comprise at least one of an interest of the user of the first device or a goal for a session.

14. The method of clause 12, wherein the phrase data transmitted to the first device comprises text of the selected phrase, input for a text-to-speech engine corresponding to the selected phrase, or audio of the selected phrase.

15. The method of clause 12, wherein the method comprises:

receiving, from the first device, additional data, wherein the additional data comprises one or more of a video stream, a location of the first device, data from a heart rate sensor, or data from a galvanic skin response sensor; and transmitting the additional data to the second device.

16. The method of clause 12, wherein the method comprises:
   storing in a data store at least one of a portion of the audio data or a transcription of a portion of the audio data; and
   storing in the data store at least one of the selected phrase, the phrase data, or an audio signal generated from the phrase data.

17. The method of clause 16, wherein the method comprises:
   storing in the data store a first timestamp corresponding to a portion of the audio data; and
   storing in the data store a second timestamp corresponding to presentation of the phrase data on the first device.

18. One or more non-transitory computer-readable media comprising computer executable instructions that, when executed, cause at least one processor to perform actions comprising:
   receiving a request from a user of a first device to speak with a character, wherein the character is associated with a text-to-speech voice;
   sending a message to a second user corresponding to the request;
   presenting the character on a display of the first device;
   obtaining an audio signal from a microphone of the first device;
   transmitting audio data to a second device, wherein the audio data is generated from the audio signal;
   receiving, from the second device, phrase data corresponding to a phrase to be spoken by the character;
   generating an audio signal using the phrase data corresponding to the phrase and the text-to-speech voice of the character; and
   causing audio to played corresponding to the audio signal.

19. The one or more computer-readable media of clause 18, the actions comprising receiving, from the user of the first device, a selection of the character from among a plurality of characters.

20. The one or more computer-readable media of clause 18, the actions comprising presenting text of the phrase on the display of the first device.

21. The one or more computer-readable media of clause 18, the actions comprising:
   obtaining text of speech of the user of the first device; and
   presenting the text of the speech of the user on the display of the first device.

22. The one or more computer-readable media of clause 18, the actions comprising:
   receiving a request from the second device to play an audio or video clip; and
   causing the audio or video clip to be presented by the first device.

23. The one or more computer-readable media of clause 18, wherein obtaining an audio signal and transmitting audio data to the second device commences after opening an application on the first device, receiving a request to speak with the character, or a selection of the character from among a plurality of characters.

24. A method for guiding the operation of an application on a first device, the method performed by a second device and comprising:
   receiving audio data, wherein the audio data represents speech of a user of the first device;
   causing audio to be played using the audio data;
   receiving a plurality of phrases as suggestions of phrases to be spoken by a character displayed on the first device;
   presenting the plurality of phrases on a display of the second device;
   receiving an input from a user of the second device that specifies a selected phrase; and
   causing phrase data to be transmitted to the first device, wherein the phrase data corresponds to the selected phrase.

25. The method of clause 24, comprising:
   receiving from the user of the second device an input requesting a second plurality of phrases as suggestions of phrases to be spoken by the character displayed on the first device;
   transmitting to a server computer a request for the second plurality of phrases;
   receiving the second plurality of phrases; and
   presenting the second plurality of phrases on the display of the second device.

26. The method of clause 24, comprising:
   receiving video data, wherein the video data represents video captured by a camera of the first device; and
   causing video to be presented by on the display of the second device.

27. The method of clause 24, wherein the plurality of phrases comprises the selected phrase.

28. The method of clause 24, wherein the audio data is received in real time.

Figure 5:
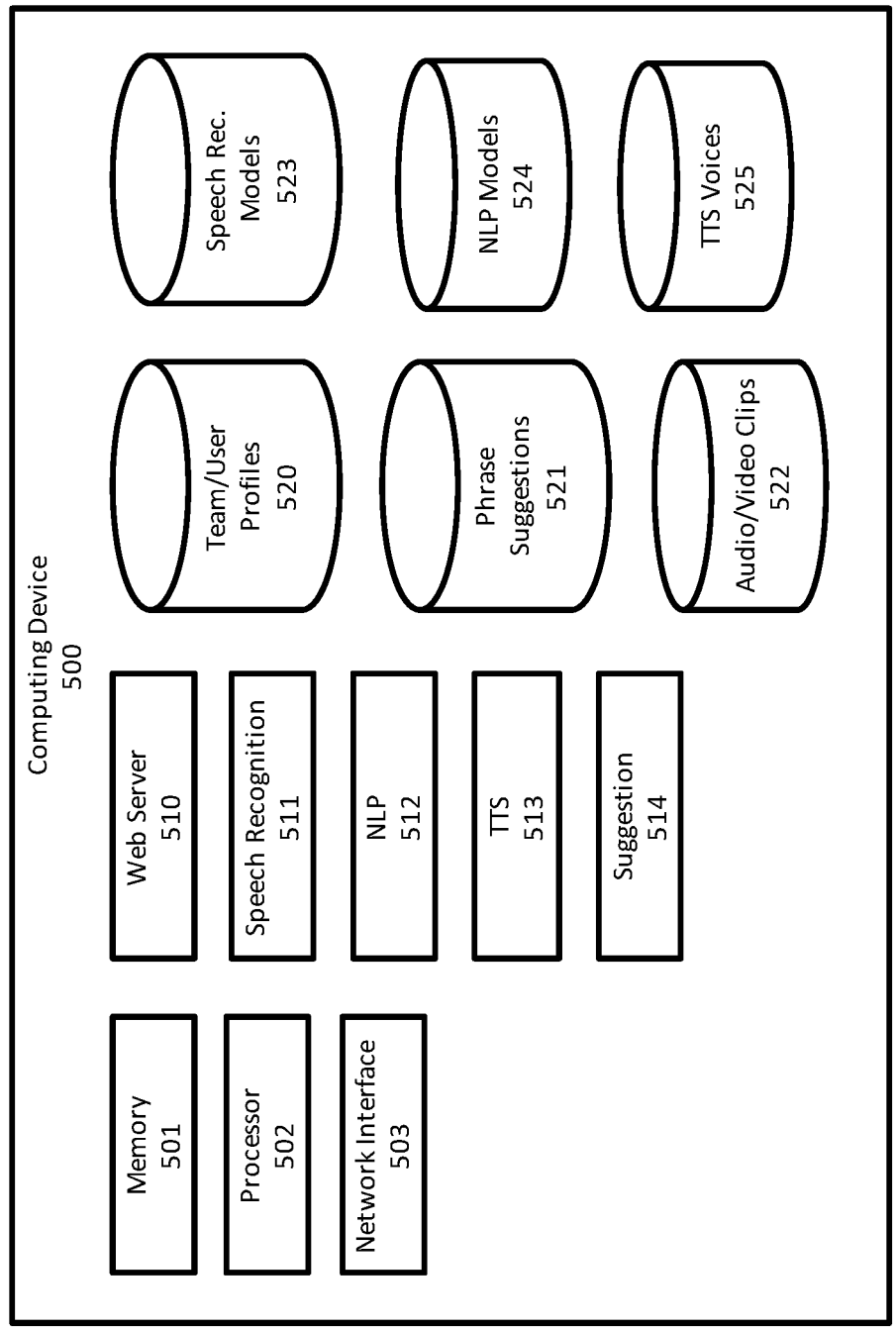
FIG. 5 illustrates components of one implementation of a computing device that may be used to guide a personal companion.

FIG. 5 illustrates components of some implementations of a computing device 500 that may be used for any of a Hero device, a guided device, a Coach device, a guiding device, or a server that operates in conjunction with any of the foregoing devices. In FIG. 5 the components are shown as being on a single computing device, but the components may be distributed among multiple computing devices, such as among any of the devices mentioned above or among several server computing devices.

Computing device 500 may include any components typical of a computing device, such one or more processors 502, volatile or nonvolatile memory 501, and one or more network interfaces 503. Computing device 500 may also include any input and output components, such as displays, keyboards, and touch screens. Computing device 500 may also include a variety of components or modules providing specific functionality, and these components or modules may be implemented in software, hardware, or a combination thereof. Below, several examples of components are described for one example implementation, and other implementations may include additional components or exclude some of the components described below.

Computing device 500 may include a web server component 510 for interacting with other devices, such as Hero device or Coach device. Web server component 510 may provide a user interface and other functionality to allow the Hero and/or Coach to interact with the Sidekicks service. Computing device 500 may include a speech recognition component 511 that may be used to recognize speech of a Hero, a Coach, or other people. The speech recognition results may be used, for example, to generate transcripts of a session or to facilitate a Coach in guiding a Sidekick. Computing device 500 may include a natural language processing (NLP) component 512, that may be used to process speech recognition results and generate NLP results indicating a meaning of the processed speech. NLP results may be used, for example, to automatically process a Hero's speech and generate suggestions adapted to the Hero's speech. Computing device 500 may include a TTS component that may be used to generate audio from provided text (or other input), for example, to provide audio to be spoken by a Sidekick. Computing device 500 may include a suggestion component 514 that provides suggestions to Coaches for phrases that may be spoken by a Sidekick as described above.

Computing device 500 may include or have access to various data stores, such as data stores 520, 521, 522, 523, 524, and 525. Data stores may use any known storage technology such as files or relational or non-relational databases. For example, computing device 500 may have team and/or user profiles data store 520 to store any of the information described above about Heroes, Coaches, and Teams. Computing device 500 may have a phrase suggestions data store 521 that may be used by suggestion component 514 in providing suggestions of phrases to a Coach. Computing device 500 may have an audio and/or video clips data store 522 that may be used to allow the Coach and/or Hero share audio and/or video clips with each other or with other Coaches and/or Heroes using the service. Computing device 500 may further have a speech recognition models data store 523 that may be used by speech recognition component 511, an NLP models data store 524 that may be used by NLP component 512, and a TTS voices data store 525 that may be used by TTS component 513.

Figure 6:
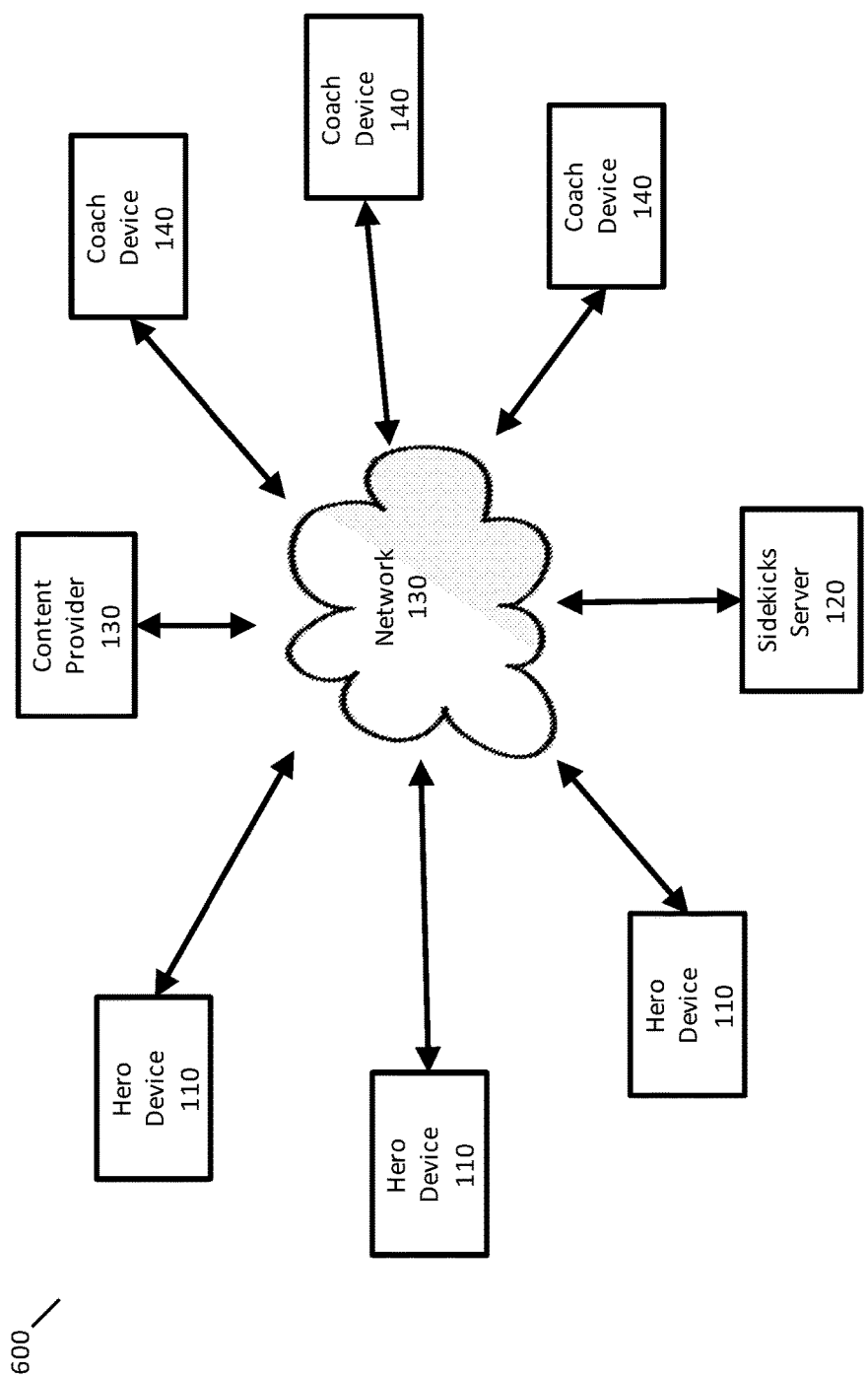
FIG. 6 illustrates a system with multiple Coaches and Heroes communicating via a guided personal companion.

FIG. 6 illustrates a system 600 that allows multiple Coaches and Heroes to communicate via a guided personal companion. System 600 includes multiple Hero devices 110 and multiple Coach devices 140 connected to network 130. Network 130 may be any network that allows multiple devices to communicate, such as the Internet or a cellular data network. A single Hero may have multiple Hero devices and may communicate with a Sidekick using different Hero devices at different times. Similarly, a single Coach may have multiple Coach devices 140 and may guide a Sidekick using different Coach devices at different times. System 600 may be used by multiple Heroes and multiple Coaches. For example, a first Hero may be interacting with a Sidekick on a first Hero device 110 where the Sidekick is being guided by a first Coach on a first Coach device 140. At the same time or at other times, a second Hero may be interacting with a Sidekick on a second Hero device 110 where the Sidekick is being guided by a second Coach using a second Coach device 140. In some instances, multiple Coaches may be guiding a single Hero or a single Coach may be guiding multiple Heroes.

System 600 includes a Sidekicks server 120. A company that provides a Sidekicks service may operate Sidekicks server 120 that is connected to network 130. Sidekicks server 120 may include one or more computers located in a data center or in multiple data centers that together provide the functionality and features herein. For example, data from a Hero device being used be a first Hero may be transmitted via network 130 to server 120, and server 120 may process the data and/or transmit the data to a Coach device of a first Coach who is currently guiding the first Hero.

System 600 may also include content provider 130, described above, that provides content to Hero devices and/or Coach devices. In some implementations, content provider 130 may be operated by the company providing the Sidekicks service and may be provided by or collocated with Sidekicks server 120. In some implementations, content provider 130 may be operated by a third party.

The system and techniques described above therefore comprise technological improvements to several underlying technologies, including (among others): the technology of back-and-forth communication between two devices through a communication network to enable a user of one of the devices to manage operation of an application on the other of the devices; the technology of providing features in a user interface that are presented to a user of a device, based on information specified by a user of a second device; the technology of providing features in a user interface that help a user of a device to coach a user of another device by means of information and commands sent from the first device to the second device. The technological improvements include (among others) enhancing a user interface at one or both of the devices to provide additional and modified features based on information and commands sent through a communication network between the first device and the second device; providing information through a communication network to a user of one of the devices that help the user in controlling the application running on the other device; providing features of the user interface on the other of the devices that enhance the familiarity, comfort, and fluidity of the interaction by a user of the other device; and providing for selected, timed and choreographed communication back and forth between the two devices that facilitates real-time or near real-time virtual interaction between users of the two devices.

Depending on the implementation, steps of any of the techniques described above may be performed in a different sequence, may be combined, may be split into multiple steps, or may not be performed at all. The steps may be performed by a general purpose computer, may be performed by a computer specialized for a particular application, may be performed by a single computer or processor, may be performed by multiple computers or processors, may be performed sequentially, or may be performed simultaneously.

The techniques described above may be implemented in hardware, in software, or a combination of hardware and software. The choice of implementing any portion of the above techniques in hardware or software may depend on the requirements of a particular implementation. A software module or program code may reside in volatile memory, non-volatile memory, RAM, flash memory, ROM, EPROM, or any other form of a non-transitory computer-readable storage medium.

Conditional language used herein, such as, "can," "could," "might," "may," "e.g.," is intended to convey that certain implementations include, while other implementations do not include, certain features, elements and/or steps. Thus, such conditional language indicates that that features, elements and/or steps are not required for some implementations. The terms "comprising," "including," "having," and the like are synonymous, used in an open-ended fashion, and do not exclude additional elements, features, acts, operations. The term "or" is used in its inclusive sense (and not in its exclusive sense) so that when used, for example, to connect a list of elements, the term "or" means one, some, or all of the elements in the list.

Conjunctive language such as the phrase "at least one of X, Y and Z," unless specifically stated otherwise, is to be understood to convey that an item, term, etc. may be either X, Y or Z, or a combination thereof. Thus, such conjunctive language is not intended to imply that certain embodiments require at least one of X, at least one of Y and at least one of Z to each be present.

While the above detailed description has shown, described and pointed out novel features as applied to various implementations, it can be understood that various omissions, substitutions and changes in the form and details of the devices or techniques illustrated may be made without departing from the spirit of the disclosure. The scope of inventions disclosed herein is indicated by the appended claims rather than by the foregoing description. All changes which come within the meaning and range of equivalency of the claims are to be embraced within their scope.

What is claimed is:

1. A system for guiding operation of an application on a first device, the system comprising the first device and a second device, wherein:

the application on the first device is configured to:
engage in a session with the second device, wherein, during the session, a second user of the second device specifies a phrase to be communicated by a character to a first user of the first device and wherein the first user of the first device and the second user of the second device participate simultaneously in the session;
present the character on the first device,
receive a first communication from the first user to the character, and
transmit the first communication to the second device;
the second device is configured to:
receive the first communication from the first device,
present the first communication to the second user,
present suggested phrases for possible communication by the character to the first user,
receive an input from the second user of the second device that specifies a phrase to be communicated by the character to the first user by receiving text entered by the second user that is different from the suggested phrases, and
cause phrase data to be transmitted to the first device corresponding to the specified phrase; and
the application on the first device is configured to:
receive the phrase data corresponding to the specified phrase, and
present a second communication to the first user corresponding to the specified phrase.

2. The system of claim 1, wherein:
the second user is a parent or caretaker of the first user; and
the second user specifies the phrase to assist the first user.

3. The system of claim 1, wherein the specified phrase comprises a modified suggested phrase.

4. The system of claim 1, wherein the input from the second user corresponds to received keyboard input or an audio signal received from a microphone connected to the second device.

5. The system of claim 1, wherein the input from the second user comprises a selection of one of the suggested phrases and an editing of the selected phrase.

6. The system of claim 1, wherein:
the application on the first device is configured to transmit audio or video data of the first user to the second device during the session; and
the second device is configured to receive the audio or video data from the first device and present the audio or video data to the second user during the session.

7. The system of claim 1, wherein:
the second device is configured to:
receive an input from the second user corresponding to an instruction to play an audio or video clip on the first device, and
send an instruction to the first device to play the audio or video clip; and
the first device is configured to:
receive the instruction to play the audio or video clip, and
cause the audio or video clip to be presented by the first device.

8. The system of claim 1, wherein the system comprises a server computer and wherein the application on the first device is configured to transmit the first communication to the second device during the session by transmitting the first communication via the server computer.

9. The system of claim 8, wherein the server computer is configured to:
receive preferences for communications with the first user;
determine the suggested phrases using the preferences; and
transmit the suggested phrases to the second device.

10. The system of claim 8, wherein the server computer is configured to:
receive a request from the first device to initiate the session; and
send a message to the second user;
wherein the second device engages in the session after the second user receives the message.

11. The system of claim 8, wherein the server computer is configured to:
receive a request from the second device to initiate the session; and
send a message to the first user;
wherein the first device engages in the session after the first user receives the message.

12. The system of claim 1, wherein the second device is configured to present a transcript of the session to the second user, and wherein the transcript comprises the first communication and the second communication.

13. One or more non-transitory computer-readable media comprising computer executable instructions that, when executed, cause at least one processor to perform actions comprising:
receiving a request from a first user of a first device to communicate with a character;
sending a message to a second user of a second device corresponding to the request;
engaging in a session with the second device, wherein, during the session, the second user of the second device specifies a phrase to be communicated by the character to the first user and wherein the first user of the first device and the second user of the second device participate simultaneously in the session;
presenting the character on the first device;
receiving a first communication from the first user to the character;
transmitting the first communication to the second device;
receiving, from the second device, phrase data corresponding to a second communication to be presented by the character to the first user by receiving text entered by the second user that is different from suggested phrases;
presenting the second communication by the character to the first user corresponding to the phrase data.

14. The one or more computer-readable media of claim 13, the actions comprising receiving, from the first user, a selection of the character from among a plurality of characters.

15. The one or more computer-readable media of claim 13, the actions comprising presenting text of the second communication on a display of the first device.

16. The one or more computer-readable media of claim 13, the actions comprising:
obtaining text of speech of the first user; and
presenting the text of the speech of the first user on a display of the first device.

17. The one or more computer-readable media of claim 13, the actions comprising:
receiving a request from the second device to play an audio or video clip; and causing the audio or video clip to be presented by the first device.

18. The one or more computer-readable media of claim 13, wherein receiving the first communication from the first user comprises obtaining an audio signal corresponding to speech of the first user received at a microphone of the first device.

19. A method for guiding operation of an application on a first device, the method performed by a second device and comprising:
- engaging in a session with the first device, wherein, during the session, a second user of the second device specifies a phrase to be communicated by a character to a first user of the first device and wherein the first user of the first device and the second user of the second device participate simultaneously in the session;
- receiving a first communication from the first device, wherein the first communication is a communication from the first user to the character;
- presenting the first communication to the second user;
- receiving suggested phrases for possible communication by the character to the first user;
- presenting the suggested phrases on a display of the second device;
- receiving an input from the second user that specifies a phrase by receiving text entered by the second user that is different from the suggested phrases; and
- causing phrase data to be transmitted to the first device, wherein the phrase data corresponds to the specified phrase.

20. The method of claim 19, comprising:
- receiving from the second user an input requesting second suggested phrases for possible communication by the character to the first user;
- transmitting to a server computer a request for the second suggested phrases;
- receiving the second suggested phrases; and
- presenting the second suggested phrases on the display of the second device.

21. The method of claim 19, comprising:
- receiving audio or video data of the first user from the first device; and
- presenting the audio or video data to the second user.

22. The method of claim 19, wherein the specified phrase comprises a modified suggested phrase.

* * * * *